US012715863B2

(12) United States Patent
Bhattacharya et al.

(10) Patent No.: US 12,715,863 B2
(45) Date of Patent: Aug. 25, 2026

(54) 5-(THIOPHEN-2-YL)-1 H-TETRAZOLE DERIVATIVE AS BCKDK INHIBITORS USEFUL FOR TREATING VARIOUS DISEASES

(71) Applicant: Pfizer Inc., New York, NY (US)

(72) Inventors: Samit Kumar Bhattacharya, Waltham, MA (US); Christopher Ryan Butler, Canton, MA (US); Kevin James Filipski, Reading, MA (US); Bethany Lyn Kormos, Somerville, MA (US); Luis Angel Martinez-Alsina, Gales Ferry, CT (US); Russell Alan Miller, Dedham, MA (US); Kiyoyuki Omoto, Bedford, MA (US); Brian Raymer, Holliston, MA (US); Matthew Richard Reese, Mystic, CT (US); Rachel Jane Roth Flach, Rockland, MA (US); Yuan Zhang, Mansfield, MA (US)

(73) Assignee: Pfizer Inc., New York, NY (US)

( * ) Notice: Subject to any disclaimer, the term of this patent is extended or adjusted under 35 U.S.C. 154(b) by 1275 days.

(21) Appl. No.: 17/619,912

(22) PCT Filed: Jun. 24, 2020

(86) PCT No.: PCT/IB2020/055974

§ 371 (c)(1),
(2) Date: Dec. 16, 2021

(87) PCT Pub. No.: WO2020/261144

PCT Pub. Date: Dec. 30, 2020

(65) Prior Publication Data

US 2022/0363673 A1 Nov. 17, 2022

Related U.S. Application Data

(60) Provisional application No. 62/960,824, filed on Jan. 14, 2020, provisional application No. 62/868,542, filed on Jun. 28, 2019.

(51) Int. Cl.

| | |
|---|---|
| ***C07D 409/04*** | (2006.01) |
| ***A61K 31/41*** | (2006.01) |
| ***A61K 45/06*** | (2006.01) |
| ***A61P 3/10*** | (2006.01) |
| ***A61P 9/04*** | (2006.01) |

(52) U.S. Cl.

CPC ........... *C07D 409/04* (2013.01); *A61K 31/41* (2013.01); *A61K 45/06* (2013.01); *A61P 3/10* (2018.01); *A61P 9/04* (2018.01); *C07B 2200/13* (2013.01)

(58) Field of Classification Search

CPC ... A61P 9/04; A61P 3/10; A61K 31/41; A61K 45/06; C07D 409/04; C07B 2200/13

See application file for complete search history.

(56) References Cited

FOREIGN PATENT DOCUMENTS

| | | |
|---|---|---|
| WO | 2017174716 | 10/2017 |
| WO | 2020/261144 A1 | 12/2020 |

OTHER PUBLICATIONS

Netchitailo, Pierre, et al. Acidic Dissociation Constants of Some 2-Substituted 3-Hydroxy-Thiophenes in Water-Dimethyl Sulfoxide Mixtures; a Comparison with the Corresponding Ortho-Substituted Phenols, Issue No. 8, pp. 196-197., 1977 (Year: 1977).*

Database Registry Chemical Abstracts Service, Columbus, Ohio, Accession No. RN 874830-71-4, Entered STN: Feb. 21, 2006 (Year: 2006).*

Chen, M., et al., "Therapeutic Effect of Targeting Branched-Chain Amino Acid Catabolic Flux in Pressure-Overloaded Indcued Heart Failure", Journal of American Heart Association, 2109, pp. 1-20, 8(11).

Du, Xiaoyu, et al., "Relationships between circulation branch chain amino acid concentratioins and risk of adverse cardiovascular events in patients with STEMI treated with PCI", Scientific Reports—Nature, 2018, pp. 1-8, 8(15809).

Ericksen, R., et al., "Loss of BCAA Catabolismduring Carcinogenesis Enhances mTORC1 Activity and Promotes Tumor Development and Progression", Cell Metabolism, May 7, 2019, pp. 1151-1165, vol. 29.

International Written Opinion and Search Report mailed on Aug. 31, 2020 for Application No. PCT/IB2020/055974, filed on Jun. 14, 2020, 16 pages.

Lian, K., et al., "PP2Cm overexpression alleviates MI/R injury medicated by a BCAA catabolismdefect and oxidative stress in diabetic mice", European Journal of Pharmacology, 2020, pp. 1-10, 866(172796).

Shih-Chia, Tso, et al., "Benzothiophene Carboxylate Derivatives as Novel Allosteric Inhibitors of Branched-chain [alpha]-Ketoacid Dehydrogenase Kinase", Journal of Biological Chemistry, Jul. 25, 2014, pp. 20583-20593, 289(30).

Shih-Chia, Tso, et al., "Structure-based design and mechanisms of allosteric inhibitors for mitochondrial branced-chain [aplph]-ketoacid dehydrogenase kinase", Proceedings of the National Academy of Sciences, Jun. 13, 2013, pp. 9728-9733, 110(24).

(Continued)

*Primary Examiner* — Samantha L Shterengarts

(74) *Attorney, Agent, or Firm* — Young-In J. Oh

(57) ABSTRACT

Described herein are compounds of Formula I,

I

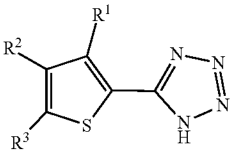

wherein $R^1$, $R^2$, and $R^3$ are defined herein, their use as branched-chain alpha keto acid dehydrogenase kinase inhibitors, pharmaceutical compositions containing such inhibitors and the use of such inhibitors to treat, for example, diabetes, NASH and heart failure.

33 Claims, 2 Drawing Sheets

(56) References Cited

OTHER PUBLICATIONS

Tian, Q., et al., "Phosphorylation of BCKDK of BCAA catabolismat Y246 by Scr promotes metastasis of colorectal cancer", Oncogen, Apr. 1, 2020, pp. 3980-3996, vol. 39.

Uddin, G.M., et al., "Impaired branched chain amino acid oxidation contributes to cardiac insulin resistance in heart failure", Cardio-vascular Diabetology, 2019, pp. 1-12, 18(86).

Wang, J., et al., "BCAA Catabolic Defect Alters Glucose Metabolism in Lean Mice", Frontiers in Physiology, Sep. 4, 2019, Article 1140, pp. 1-14, vol. 10.

International Preliminary Report on Patentability mailed on Jan. 6, 2022 for WO Application No. PCT/IB2020/055974, 7 pages.

* cited by examiner

5-(THIOPHEN-2-YL)-1 H-TETRAZOLE DERIVATIVE AS BCKDK INHIBITORS USEFUL FOR TREATING VARIOUS DISEASES

This application is a national stage application under 35 U.S.C. 371 of PCT//IB2020/055974, filed on Jun. 24, 2020, which claims the benefit of U.S. Provisional Patent Application No. 62/960,824, filed on Jan. 14, 2020, and U.S. Provisional Patent Application No. 62/868,542, filed Jun. 28, 2019, the disclosures of which are hereby incorporated by reference in their entirety.

FIELD OF THE INVENTION

The present invention provides compounds that are branched-chain alpha keto acid dehydrogenase kinase inhibitors, pharmaceutical compositions containing such inhibitors and the use of such inhibitors to treat for example, diabetes, NASH and heart failure.

BACKGROUND OF THE INVENTION

Branched-chain amino acids (BCAAs) account for about 40% of the essential amino acids in healthy subjects and must be acquired through a well-balanced diet. Branched-chain amino acids are toxic in excess but are required for protein synthesis and cellular signaling processes. BCAAs are transaminated by branched-chain aminotransferase (BCAT) to their alpha-keto acid forms: alpha-ketoisocaproate (KIC/ketoleucine), 2-keto-3-methylvalerate (KMV/ketoisoleucine) and alpha-ketoisovalerate (KIV/ketovaline). The branched-chain keto acids (BCKAs) are then oxidatively decarboxylated by the branched-chain ketoacid dehydrogenase (BCKDH) enzyme complex, which consists of multiple copies of BCKDH E1$\alpha$/$\beta$ tetramers, BCKDH E2, and BCKDH E3 subunits. The complex is regulated by inhibitory phosphorylation, which is mediated by BCKDH kinase (BCKDK), and this same phosphorylation site is dephosphorylated by the phosphatase PPM1K. Inhibition of complex phosphorylation promotes BCKDH activity and thus the irreversible catabolism of BCKA. (Lynch C J, Adams S H: Branched-chain amino acids in metabolic signalling and insulin resistance. Nat Rev Endocrinol 2014, 10:723-36.) Deletion of Bckdk in mice confirms this regulation as mice lacking Bckdk display increased BCKDH activity in multiple tissues. (Joshi M A, Jeoung N H, Obayashi M, Hattab E M, Brocken E G, Liechty E A, Kubek M J, Vattem K M, Wek R C, Harris R A: Impaired growth and neurological abnormalities in branched-chain alpha-keto acid dehydrogenase kinase-deficient mice. Biochem J 2006, 400:153-62.)

U.S. Pat. No. 9,078,865 is directed to for example, methods of decreasing plasma levels of one or more branched-chain amino acids or branched-chain alpha-ketoacids comprising administering to an individual in need thereof a therapeutically effective amount of at least one compound of the formula: phenyl-$CH_2$—$(CH_2)_n$—COOH wherein n is 0, 2, 4, 6 or 8 in order to treat for example an inborn error of metabolism in newborns known as maple syrup urine disease (MSUD). MSUD, also called branched-chain ketoaciduria, is an autosomal recessive disorder.

There is a strong correlation with BCAA catabolism and cardiometabolic health. Increased BCAA/BCKA levels have been observed in plasma of type 2 diabetic patients in multiple studies. (Wang T J, Larson M G, Vasan R S, Cheng S, Rhee E P, McCabe E, Lewis G D, Fox C S, Jacques P F, Fernandez C, O'Donnell C J, Carr S A, Mootha V K, Florez J C, Souza A, Melander O, Clish C B, Gerszten R E: Metabolite profiles and the risk of developing diabetes. Nat Med 2011, 17:448-53; Newgard C B, An J, Bain J R, Muehlbauer M J, Stevens R D, Lien L F, Haqq A M, Shah S H, Arlotto M, Slentz C A, Rochon J, Gallup D, Ilkayeva O, Wenner B R, Yancy W S, Jr., Eisenson H, Musante G, Surwit R S, Millington D S, Butler M D, Svetkey L P: A branched-chain amino acid-related metabolic signature that differentiates obese and lean humans and contributes to insulin resistance. Cell Metab 2009, 9:311-26.)

Reduced PPM1K and increased BCKDK levels were observed in human NASH. (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human nonalcoholic fatty liver disease. Amino Acids 2015, 47:603-15.)

Reduced mRNA levels for enzymes in the catabolic pathway have also been observed in skeletal muscle of human diabetic patients. (Lerin C, Goldfine A B, Boes T, Liu M, Kasif S, Dreyfuss J M, De Sousa-Coelho A L, Daher G, Manoli I, Sysol J R, Isganaitis E, Jessen N, Goodyear L J, Beebe K, Gall W, Venditti C P, Patti M E: Defects in muscle branched-chain amino acid oxidation contribute to impaired lipid metabolism. Mol Metab 2016, 5:926-36.)

Similarly, metabolomics and RNA profiling data from mouse hearts also suggest that genes in the BCAA/BCKA catabolic pathway are downregulated in heart failure. (Lai L, Leone T C, Keller M P, Martin O J, Broman A T, Nigro J, Kapoor K, Koves T R, Stevens R, Ilkayeva O R, Vega R B, Attie A D, Muoio D M, Kelly D P: Energy metabolic reprogramming in the hypertrophied and early stage failing heart: a multisystems approach. Circ Heart Fail 2014, 7:1022-31; Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

These data collectively suggest that BCAA catabolism is impaired in multiple human disease states. One mechanism to increase BCAA catabolism is a BCKDK inhibitor. By inhibiting BCKDK, BCKDH activity will increase and BCAA catabolism will be increased. Although there has been some early research related to BCKDK there remains a need for pharmaceutical agents that have BCKDK inhibiting activity and are useful in the treatment, prevention or diminution of the manifestations of the maladies described herein.

SUMMARY OF THE INVENTION

The present invention is directed to compounds of the Formula I

Formula I

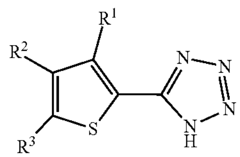

wherein $R^1$ is fluoro, chloro, bromo, hydroxyl, amino, cyano, ethynyl, $(C_1\text{-}C_4)$alkyl, $(C_3\text{-}C_4)$cycloalkyl, $(C_1\text{-}C_4)$alkoxy, $(C_1\text{-}C_4)$fluoroalkyl or $(C_1\text{-}C_4)$fluoroalkoxy; wherein when $R^2$ is H and $R^3$ is H, $R^1$ is fluoro, chloro, amino, cyano, ethynyl, $(C_2\text{-}C_4)$alkyl, $(C_3\text{-}C_4)$cycloalkyl, $(C_1\text{-}C_4)$alkoxy, $(C_1\text{-}C_4)$fluoroalkyl or $(C_1\text{-}C_4)$fluoroalkoxy;

$R^2$ is H, fluoro, chloro, bromo, hydroxyl, amino, cyano, ethynyl, $(C_1\text{-}C_4)$alkyl, $(C_3\text{-}C_4)$cycloalkyl, $(C_1\text{-}C_4)$alkoxy, $C_1\text{-}C_4)$fluoroalkyl, or $(C_1\text{-}C_4)$fluoroalkoxy;

$R^3$ is H, fluoro, chloro, bromo, hydroxyl, amino, cyano, ethynyl, $(C_1\text{-}C_4)$alkyl, $(C_3\text{-}C_4)$cycloalkyl, $(C_1\text{-}C_4)$alkoxy, $(C_1\text{-}C_4)$fluoroalkyl or $(C_1\text{-}C_4)$fluoroalkoxy;

or a pharmaceutically acceptable salt of said compound.

The present invention is also directed at methods of treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount of a compound of Formula I or a pharmaceutically acceptable salt of said compound.

The present invention is also directed at methods of treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

The present invention is also directed at methods of treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula I or a pharmaceutically acceptable salt of said compound.

The present invention is also directed at methods of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

The present invention is also directed at pharmaceutical compositions having a therapeutically effective amount of a compound of Formula I or a pharmaceutically acceptable salt of said compound and a pharmaceutically acceptable carrier, vehicle or diluent.

The present invention is also directed at pharmaceutical combination compositions that include: a therapeutically effective amount of a composition having:

a first compound, said first compound being a compound of Formula I or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluent.

It is to be understood that both the foregoing general description and the following detailed description are exemplary and explanatory only and are not restrictive of the invention, as claimed.

DETAILED DESCRIPTION OF THE INVENTION

Figure 1:
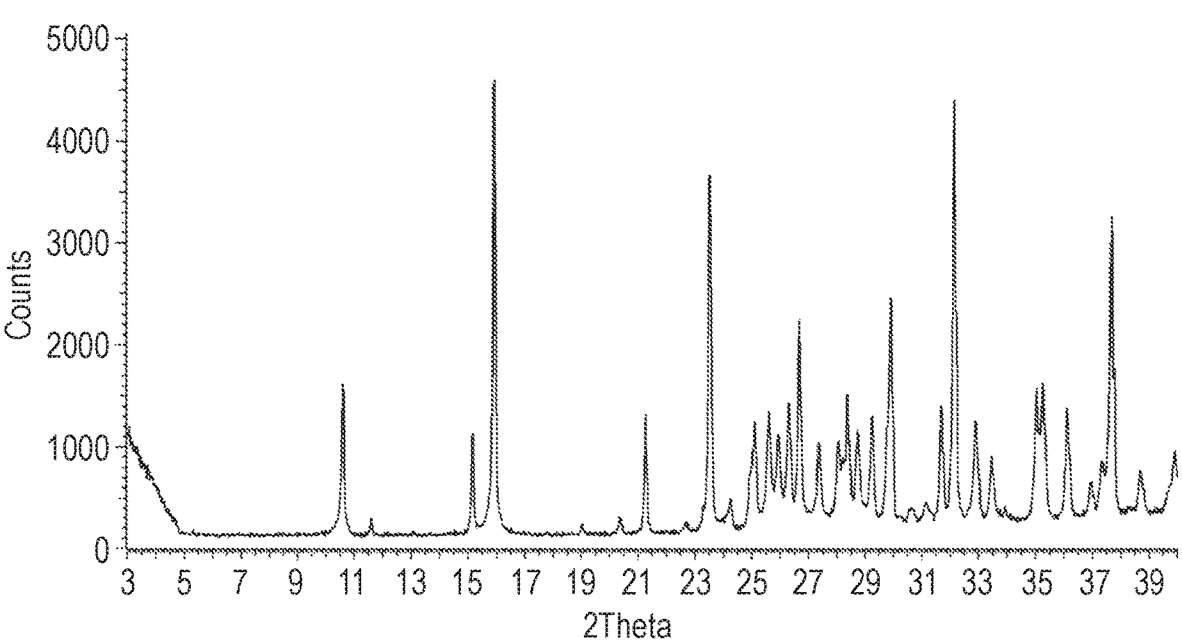
FIG. 1 is a characteristic x-ray powder diffraction pattern showing a crystalline form of Example 6, Form 1 (Vertical Axis: Intensity (CPS); Horizontal Axis: Two theta (degrees)).

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

The term "alkyl", alone or in combination, means an acyclic, saturated hydrocarbon group of the formula CnH2n+1 which may be linear or branched. Examples of such groups include methyl, ethyl, n-propyl, isopropyl, butyl, sec-butyl, isobutyl and t-butyl. The carbon atom content of alkyl and various other hydrocarbon-containing moieties is indicated by a prefix designating a lower and upper number of carbon atoms in the moiety, that is, the prefix Ci-Cj indicates a moiety of the integer “i” to the integer “j” carbon atoms, inclusive. Thus, for example, $C_1$-$C_3$ alkyl refers to alkyl of one to three carbon atoms, inclusive.

“Fluoroalkyl” means an alkyl as defined herein substituted with one, two or three fluoro atoms. Exemplary ($C_1$)fluoroalkyl compounds include fluoromethyl, difluoromethyl and trifluoromethyl; exemplary ($C_2$)fluoroalkyl compounds include 1-fluoroethyl, 2-fluoroethyl, 1,1-difluoroethyl, 1,2-difluoroethyl, 1,1,1-trifluoroethyl, 1,1,2-trifluoroethyl, and the like.

“Cycloalkyl” refers to a nonaromatic ring that is fully hydrogenated group of the formula CnH2n−1. Examples of such carbocyclic rings include cyclopropyl and cyclobutyl.

By “alkoxy” is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

By “fluoroalkoxy” means an alkoxy as defined herein substituted with one, two or three fluoro atoms. Exemplary ($C_1$)fluoroalkoxy compounds include fluoromethoxy, difluoromethoxy and trifluoromethoxy; exemplary ($C_2$)fluoroalkyl compounds include 1-fluoroethoxy, 2-fluoroethoxy, 1,1-difluoroethoxy, 1,2-difluoroethoxy, 1,1,1-trifluoroethoxy, 1,1,2-trifluoroethoxy, and the like.

“Compounds” when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression “prodrug” refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

As used herein, an arrowhead, “” or wavy line, “” denotes a point of attachment of a substituent to another group.

The term “mammal” refers to human, livestock or companion animals.

The term “companion animal” or “companion animals” refers to animals kept as pets or household animal. Examples of companion animals include dogs, cats, and rodents including hamsters, guinea pigs, gerbils and the like, rabbits, ferrets.

The term “livestock” refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits.

“Patient” refers to warm blooded animals such as, for example, guinea pigs, mice, rats, gerbils, cats, rabbits, dogs, cattle, goats, sheep, horses, monkeys, chimpanzees, and humans.

The term “treating” or “treatment” means an alleviation of symptoms associated with a disease, disorder or condition, or halt of further progression or worsening of those symptoms. Depending on the disease and condition of the patient, the term “treatment” as used herein may include one or more palliative treatment. Treatment can also include administering a pharmaceutical formulation of the present invention in combination with other therapies.

“Therapeutically effective amount” means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term “pharmaceutically acceptable” means the substance (e.g., the compounds of the invention) and any salt thereof, or composition containing the substance or salt of the invention that is suitable for administration to a patient.

In one embodiment, the present invention includes compounds of Formula I wherein $R^2$ is H or a pharmaceutically acceptable salt thereof.

In another embodiment, the present invention includes compounds of Formula I wherein $R^1$ is fluoro, chloro, bromo, ($C_1$-$C_2$)alkyl, or ($C_1$-$C_2$)fluoroalkyl or a pharmaceutically acceptable salt thereof.

In another embodiment, the present invention includes compounds of Formula I wherein $R^3$ is fluoro, chloro, or bromo or a pharmaceutically acceptable salt thereof.

In another embodiment, the present invention includes compounds of Formula I wherein $R^3$ is chloro or a pharmaceutically acceptable salt thereof.

In another embodiment, the present invention includes compounds of Formula I wherein $R^3$ is fluoro, chloro, or bromo or a pharmaceutically acceptable salt thereof.

In another embodiment, the present invention includes compounds of Formula I wherein $R^3$ is H or a pharmaceutically acceptable salt thereof.

In another embodiment, the present invention includes compounds of Formula I wherein $R^1$ is fluoro, chloro, bromo ($C_1$-$C_2$)alkyl, or ($C_1$-$C_2$)fluoroalkyl or a pharmaceutically acceptable salt thereof.

In another embodiment, the present invention includes compounds of Formula I wherein $R^2$ is fluoro, chloro, or bromo or a pharmaceutically acceptable salt thereof.

In another embodiment, the present invention includes compounds selected from the group consisting of:

5-(5-chloro-4-fluoro 3-methylthiophen-2-yl)-1H-tetrazole;
5-(5-chloro-3-difluoromethylthiophen-2-yl)-1H-tetrazole;
5-(5-fluoro-3-methylthiophen-2-yl)-1H-tetrazole;
5-(5-chloro-3-methylthiophen-2-yl)-1H-tetrazole;
5-(3,5-dichlorothiophen-2-yl)-1H-tetrazole;

5-(4-bromo-3-methylthiophen-2-yl)-1H-tetrazole;
5-(4-bromo-3-ethylthiophen-2-yl)-1H-tetrazole; and
5-(4-chloro-3-ethylthiophen-2-yl)-1H-tetrazole;
or a pharmaceutically acceptable salt thereof.

Another embodiment of the present invention of the present invention includes compounds having the structure

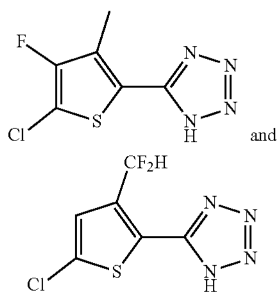

and and crystals including said compounds or pharmaceutically acceptable salts thereof.

Another embodiment of the present invention includes use of a compound of Formula I or a pharmaceutically acceptable salt of said compound for use as a medicament in treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula I or a pharmaceutically acceptable salt of said compound for the manufacture of a medicament in treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula I or a pharmaceutically acceptable salt of said compound for use as a medicament in treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for use as a medicament in treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for use as a medicament in treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{31}C$, fluorine, such as $^{18}F$, nitrogen, such as $^{13}N$ and $^{15}N$, oxygen, such as $^{15}O$, $^{17}O$ and $^{18}O$, and sulphur, such as $^{35}S$.

Certain isotopically-labelled compounds of Formula I for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$ $^{18}F$, $^{15}O$ and $^{13}N$, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagents in place of the non-labelled reagent previously employed.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Salts encompassed within the term "pharmaceutically acceptable salts" refer to the compounds of this invention which are generally prepared by reacting the free base or free acid with a suitable organic or inorganic acid, or a suitable organic or inorganic base, respectively, to provide a salt of the compound of the invention that is suitable for administration to a patient. Base salts are preferred, however, some compounds may also form acid salts. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, calcium, choline, diethylamine, glycine, lysine, magnesium, meglumine, olamine, potassium, sodium, trimethamine and zinc salts. Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002).

Hemisalts of acids and bases may also be formed, for example, hemisulfate and hemicalcium salts. For a review on suitable salts, see *Handbook of Pharmaceutical Salts: Properties, Selection*, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

Also included within the scope of the invention are active metabolites of compounds of Formula I (including prodrugs), that is, compounds formed in vivo upon administration of the drug, often by oxidation or dealkylation. Some examples of metabolites in accordance with the invention include:

(i) where the compound of Formula I contains a methyl group, a hydroxymethyl derivative thereof ($-CH_3 \rightarrow -CH_2OH$) and (ii) where the compound of Formula I contains an alkoxy group, a hydroxy derivative thereof ($-OR \rightarrow -OH$).

The compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

The term "room temperature or ambient temperature" means a temperature between 18 to 25° C., "HPLC" refers to high-pressure liquid chromatography, "MPLC" refers to medium-pressure liquid chromatography, "TLC" refers to thin-layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to 1,2-dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethyl azodicarboxylate, and "DIAD" refers to diisopropyl azodicarboxylate.

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section. Specific synthetic schemes for preparation of the compounds of Formula I are outlined below. Note that tetrazoles are generally a high energy functional group and care should be taken in the synthesis and handling of tetrazole containing molecules.

As used herein, the expressions "reaction-inert solvent" and "inert solvent" refer to a solvent or a mixture thereof which does not interact with starting materials, reagents, intermediates or products in a manner which adversely affects the yield of the desired product.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-tert-butoxycarbonyl, benzyloxycarbonyl, and 9-fluorenylmethylenoxycarbonyl for amines and lower alkyl or benzyl esters for carboxylic acids), which are generally not chemically reactive under the reaction conditions described and can typically be removed without chemically altering other functionality in the Formula I compound.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the tetrazole moiety where the proton may migrate between the four ring nitrogen as follows.

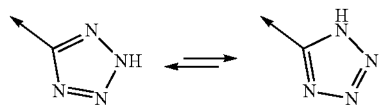 [SMILES: c1nn[nH]n1 ; c1nnn[nH]1]

Valence tautomers include interconversions by reorganization of some of the bonding electrons.

Included within the scope of the claimed compounds present invention are all stereoisomers, geometric isomers and tautomeric forms of the compounds of Formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Compounds of Formula I may be prepared according to the General Schemes and Examples provided herein.

General Schemes

Compounds of Formula I may be prepared according to Schemes I-IX.

Scheme 1

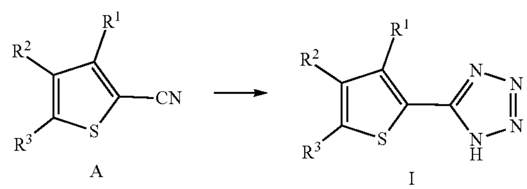

Those skilled in the art will recognize that there are a variety of methods for tetrazole formation. A Formula I tetrazole compound wherein $R^1$, $R^2$ and $R^3$ are as described above may be prepared from a Formula A nitrile by a cyclization reaction with an appropriate azide source. Conditions for this transformation include but are not limited to the reaction of a nitrile with an organic, organometallic or organosilicon azide, with or without a Lewis or Brønsted acid including the following exemplary procedures. The Formula A nitrile is cyclized to the corresponding Formula I for example, by reaction with azidotributylstannane, or with sodium azide in the presence of an amine salt such as triethylamine hydrochloride or preferably pyridine hydrochloride. Suitable aprotic solvents include nitrobenzene, toluene, NMP and preferably DMF. Alternately, the cyclization can be catalyzed by Lewis acids including copper sulfate, zinc bromide, or preferably zinc chloride, in a suitable polar solvent such as DMF, water, or preferably alcohols such as propanol. The reaction is heated at a temperature of about 25° C. to about 120° C., typically about 90° C., for about four hours to about 48 hours, typically about 12 hours.

Scheme II

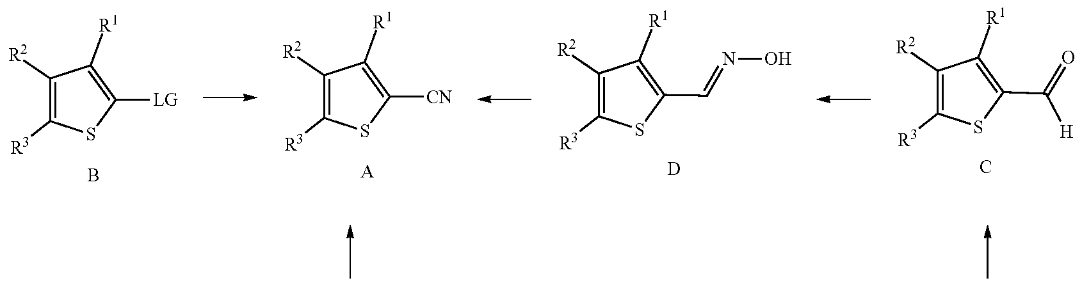

-continued

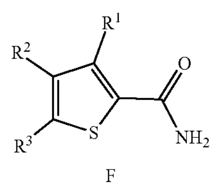

F

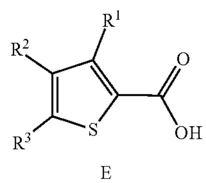

E

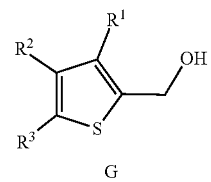

G

The Formula A nitrile may be prepared by a variety of methods including the exemplary procedures in Scheme II. A Formula A nitrile may be prepared for example from a Formula B thiophene halide, a Formula C aldehyde, a Formula D oxime, a Formula E acid or other precursors known to those skilled in the art.

The Formula A nitrile is prepared from a corresponding compound of Formula B where LG is a suitable leaving group such as a halogen, for example chloride, bromide, iodide, or sulfonate, by reaction with a cyanide source such as copper cyanide, or preferably zinc cyanide in the presence of a suitable catalyst-ligand combination such as tetrakis (triphenylphosphine)palladium(0) in a suitable solvent such as a polar, aprotic solvent such as DMF with heating from about 50° C. to about 150° C., usually around 115° C., for a period of about 2 to 24 hours, usually about 16 hours.

The Formula A nitrile may also be prepared for example from dehydration of an oxime of Formula D. This can be accomplished by a variety of reagents including acetic anhydride, trifluoroacetic anhydride, phosphoryl chloride or preferably thionyl chloride, in a range of solvents, including acetonitrile, DCM, DMF or toluene. The reaction may proceed at room temperature or the reaction may be heated up to the refluxing temperature of the appropriate solvent. Suitable reaction times are typically between about 20 minutes and 48 hours. Oximes of Formula D may in turn be prepared from aldehydes of Formula C via condensation with a hydroxylamine source such as hydroxylamine hydrochloride. The reaction take place in a variety of suitable solvents including polar solvents such as water, ethanol, DMF or NMP and a suitable base such as pyridine may be used. The reaction can occur at room temperature or the reaction may be heated up to the refluxing temperature of the appropriate solvent. Suitable reaction times are typically between about 20 minutes and 48 hours.

The requisite aldehydes of Formula C may be prepared by a variety of methods known to one skilled in the art including, but not limited to, the oxidation of a corresponding alcohol. For instance, compounds of Formula G can be oxidized by a variety of conditions including Dess-Martin periodinane, pyridinium chlorochromate, or preferably manganese(IV) oxide in a variety of solvents including acetonitrile, ethyl acetate, THF or preferably DCM at a temperature of about 0° C. to about 70° C., preferably about room temperature, over a period of about 1 to 48 hours.

Alternately, nitriles of Formula A can be prepared via dehydration of amides of Formula F using a variety of reagents including cyanuric trichloride, Burgess' reagent, thionyl chloride, phosphoryl chloride, or preferably trifluoroacetic acid anhydride in the presence of a base such as pyridine. When a solvent is used, suitable solvents include THF, DMF, or preferably DCM. Suitable temperatures for the aforesaid reaction are typically between 0° C. and 100° C. Suitable reaction times are typically from about 20 minutes to 48 hours. The amides of Formula F can be conveniently prepared from the corresponding Formula E acids by reaction under a variety of conditions including 1,1'-carbonyldiimidazole in a suitable polar, aprotic solvent such as DMF at a temperature between about 0° C. and 100° C., preferably ambient temperature, for about 1 hour to about 24 hours, preferably about 2 hours. It will be apparent to those skilled in the art that there are other ways to effect this transformation in addition to those described.

Scheme III

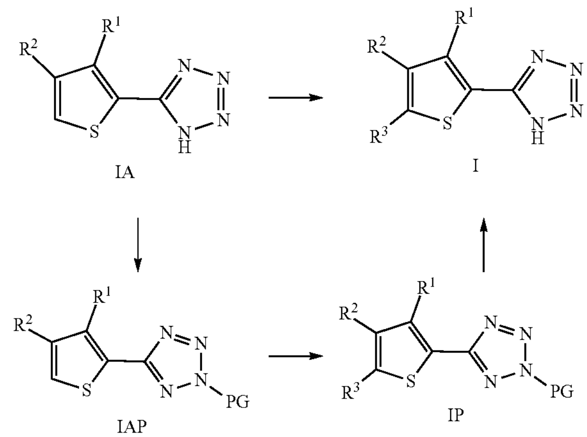

IA I IAP IP

For compounds of the Formula IA, additional derivatization may be performed after the aforementioned tetrazole cyclization. For example, compounds of the Formula IA may be halogenated by a variety of methods available to one skilled in the art. For example, compounds of Formula I where $R^3$ is Cl (or Br) may be prepared using a suitable reagent such as N-chlorosuccinimide (or N-bromosuccinimide) in a variety of suitable polar solvents such as acetic acid, acetonitrile, or preferably DMF. Suitable temperatures for the reaction are between about 0° C. and 100° C., preferably about 50° C. Reaction times are from about 2 to about 48 hours, typically about 16 hours.

Such derivatization can also be performed using an appropriate base such as n-butyllithium or LDA followed by the addition of an electrophile such as N-halosuccinimide, 1,2-dibromoethane, N-fluoro-N-(phenylsulfonyl)benzenesulfonamide, chloroformates, alkyl halides or formyl source such as DMF in a suitable polar, aprotic solvent such as THF. Suitable temperatures to run the reaction are between about −100° C. and room temperature, typically around −78° C. with warming to room temperature over time. Suitable reaction times are between about 1 to about 24 hours. In some cases, it may be desirable to protect the tetrazole group prior to derivatization. Thus, for the compound of Formula IAP in Scheme III, PG is an appropriate amine protecting group such as a trityl group. It should be noted that depending on the choice of protecting groups, the site of tetrazole protection may be at N1 or N2 or a mixture of N1 and N2. The protecting group may be installed using procedures known in the art such as reaction with triphenylmethyl chloride in the presence of an appropriate base such as triethylamine, in an appropriate aprotic solvent such as DCM. Derivatization as above affords compounds of the Formula IP, which upon deprotection give compounds of the Formula I. The deprotection is achieved by a variety of methods available to those skilled in the art. For example, compounds of the Formula IP where PG refers to trityl protection may be deprotected with trifluoroacetic acid and triethylsilane in a suitable aprotic solvent such as DCM at a temperature from about −30° C. to about 80° C., preferably about room temperature over a period of about 10 minutes to 24 hours, typically about 1 hour.

Scheme IV

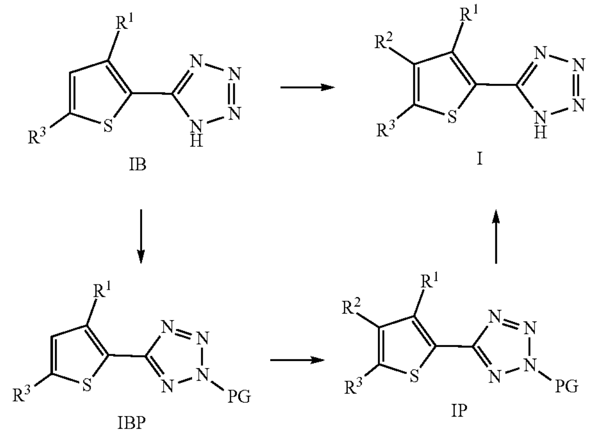

IB, I, IBP, IP

Similarly, for compounds of the Formula IB additional derivatization may be performed after the aforementioned tetrazole cyclization by a variety of methods available to one skilled in the art. For example, such derivatization can be performed using an appropriate base such as n-butyllithium or LDA followed by the addition of an electrophile such as N-halosuccinimide, 1,2-dibromoethane, N-fluoro-N-(phenylsulfonyl)benzenesulfonamide, or other alkylating agents such as alkyl halides, chloroformates or formylating reagents such as DMF or formyl piperidine in a suitable polar, aprotic solvent such as THF. Suitable temperatures to run the reactions are between about −100° C. and room temperature, typically around −78° C. with warming to room temperature over time. Suitable reaction times are between about 1 to about 24 hours. Many of the resulting products of these reactions can be further derivatized. For example, an aldehyde thus generated could itself be subject to reduction, oxidation, difluorination or other transformations known to those skilled in the art. In some cases, it may be desirable to protect the tetrazole group prior to derivatization. Thus, for the compound of Formula IBP in Scheme IV, PG is an appropriate amine protecting group such as a trityl group. The protecting group may be installed using procedures known in the art such as reaction with triphenylmethyl chloride in the presence of an appropriate base, such as triethylamine in an appropriate aprotic solvent such as DCM. Derivatization as above affords compounds of the Formula IP, which upon deprotection give compounds of the Formula I. The deprotection is achieved by a variety of methods available to those skilled in the art. For example, compounds of the Formula IP where PG refers to trityl protection may be deprotected with trifluoroacetic acid and triethylsilane in a suitable solvent such as DCM at a temperature from about −30° C. to about 80° C., preferably about room temperature over a period of about 10 minutes to 24 hours, typically about 1 hour.

Compounds of Formula A can be further elaborated prior to tetrazole formation by a variety of methods known to those skilled in the art. Such transformations include but are not limited to the examples as shown in Schemes V, VI and VII. In certain instances, a combination of two or more of these general approaches, or portions thereof, can be combined to gain access to thiophene nitriles of Formula A.

Scheme V

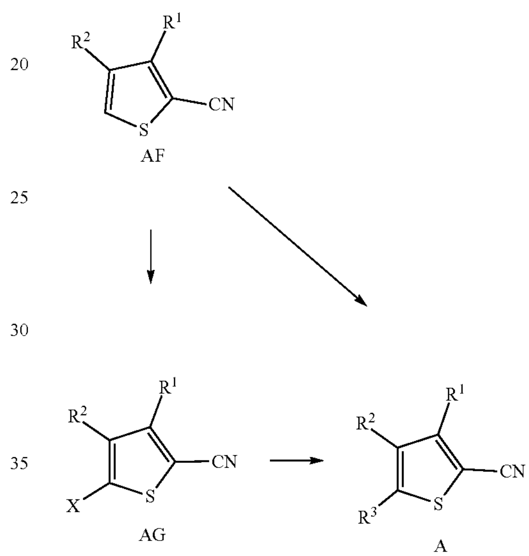

AF, AG, A

For example, for compounds of Formula AF additional derivatization may be performed prior to tetrazole cyclization. For example, compounds of the Formula AF may be halogenated by a variety of methods available to one skilled in the art. For example, compounds of Formula I where $R^3$ is Cl (or Br) may be prepared using a suitable reagent such as N-chlorosuccinimide (or N-bromosuccinimide) in a variety of suitable polar solvents such as acetic acid, acetonitrile, or preferably DMF. Suitable temperatures for the reaction are between about 0° C. and 100° C., preferably about 50° C. Reaction times are from about 2 to about 48 hours, typically about 16 hours.

Compounds of Formula AG or Formula A may also be prepared from compounds of Formula AF using an appropriate base such as n-butyllithium or LDA followed by the addition of an electrophile such as N-halosuccinimide, 1,2-dibromoethane, N-fluoro-N-(phenylsulfonyl)benzenesulfonamide, chloroformates, alkyl halides or formyl sources such as DMF in a suitable polar, aprotic solvent such as THF. Suitable temperatures to run the reactions are between about −100° C. and room temperature, typically around −78° C. with warming to room temperature over time. Suitable reaction times are between about 1 to about 24 hours. It will be apparent to those skilled in the art that many of these derivatives may themselves be suitable for further manipulation to access additional compounds of Formula A.

Scheme VI

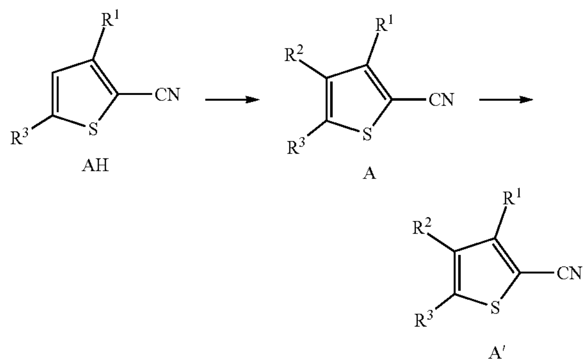

AH A A'

In a similar manner, derivatization may also be performed on compounds of Formula AH using an appropriate base such as n-butyllithium or LDA followed by the addition of an electrophile such as N-halosuccinimide, 1,2-dibromoethane, N-fluoro-N-(phenylsulfonyl)benzenesulfonamide, chloroformates, alkyl halides or formyl source such as DMF in a suitable polar, aprotic solvent such as THF. Suitable temperatures to run the reactions are between about −100° C. and room temperature, typically around −78° C. with warming to room temperature over time. Suitable reaction times are between about 1 to about 24 hours. It will be apparent to those skilled in the art that many of these derivatives may themselves be suitable for further manipulation to access additional compounds of Formula A. For example, an $R^2$ bromide could be further converted to an $R^2$ chloride with a reagent such as copper chloride in an appropriate polar, aprotic solvent such as DMF. Suitable reaction temperatures are about 50° C. to about 200° C., typically about 140° C. for about 2 hours to about 48 hours, typically about 24 hours.

Scheme VII

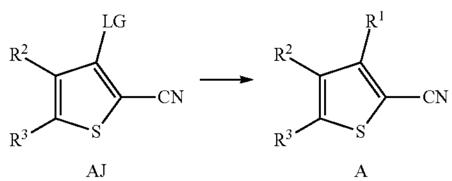

AJ A

Compounds of Formula AJ, where LG is a suitable leaving group such as a bromide or an iodide may be precursors to compounds of additional variation at $R^1$ through a variety of reactions, including but not limited to the following exemplary procedures. For example, compounds of Formula A, where $R^1$ is alkyl can be prepared from compounds of Formula AJ. Suitable conditions for this reaction include transition metal-catalyzed, preferably palladium-catalyzed coupling reactions with an appropriate coupling partner such as a potassium alkyltrifluoroborate in the presence of a suitable base such as cesium carbonate. The reaction is performed in a suitable aprotic solvent such as toluene from a temperature of about room temperature to about 120° C., preferably about 100° C. Suitable reaction time is about 1 hour to about 48 hours, typically about 24 hours.

Thiophene nitrile precursors may also be derivatized prior to preparing compounds of Formula A according to Scheme II. There are numerous starting materials and methods available to one skilled in the art, including but not limited to those depicted in Schemes VIII and IX and the following exemplary procedures.

Scheme VIII

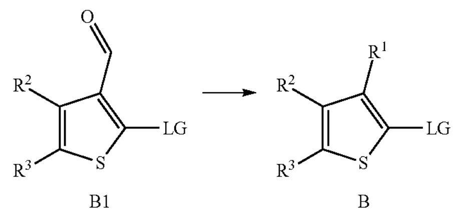

B1 B

Aldehydes of Formula B1 can be subjected to a variety of modifications including reduction, olefination, difluorination or other transformations known to those skilled in the art. For example, the aldehyde group in compounds of the Formula B1 can be converted to a difluoromethyl group using a reagent such as (diethylamino)sulfur trifluoride in a suitable aprotic solvent such as DCM. Suitable temperatures for the reaction are from about 0° C. to the temperature at which the solvent refluxes, typically about room temperature. Suitable times for this reaction are from about 1 hour to about 48 hours, typically about 16 hours.

Scheme IX

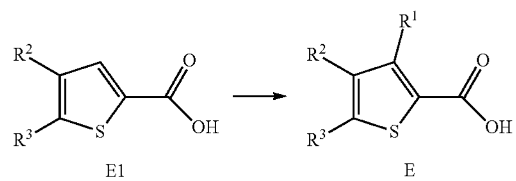

E1 E

Nitrile precursors such as carboxylic acids of Formula E may also be further elaborated prior to their conversion to nitriles as in Scheme II. For example in Scheme IX, compounds of Formula E can be prepared from compounds of Formula E1 by reaction with an appropriate strong base such as n-butyllithium, followed by addition of electrophiles including but not limited to carbonyl compounds such as DMF or acetaldehyde, alkyl halides or an N-halosuccinimide in a suitable polar, aprotic solvent such as THF. Suitable reaction temperatures are from about −80° C. to about room temperature, preferably about −70° C. for a period of about 1 to 12 hours, typically about 3 hours, followed by a period of warming to about room temperature and additional reaction time of about 1 to 24 hours.

The starting materials and reagents for the above described Formula I compounds are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

The present invention is also directed at pharmaceutical compositions having a therapeutically effective amount of a compound of Formula I or a pharmaceutically acceptable salt of said compound and a pharmaceutically acceptable carrier, vehicle or diluent.

The compounds of this invention may also be used in conjunction with other pharmaceutical agents (e.g., antiatherosclerotic and antithrombotic agents) for the treatment of the disease/conditions described herein. The present invention is also directed at pharmaceutical combination compositions that include: a therapeutically effective amount of a composition having:

a first compound, said first compound being a compound of any of Formula I or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluents.

In one embodiment of the present invention, said non-alcoholic steatohepatitis treatment agent or non-alcoholic fatty liver disease treatment agent is an ACC inhibitor, a KHK inhibitor, a DGAT-2 inhibitor, an FXR agonist, metformin, incretin analogs, or an incretin receptor modulator.

In another embodiment of the present invention, said anti-diabetic agent is an SGLT-2 inhibitor, metformin, incretin analogs, an incretin receptor modulator, a DPP-4 inhibitor, or a PPAR agonist.

In another embodiment of the present invention, said anti-diabetic agent is metfomin, sitagliptin or ertuglifozin.

In another embodiment of the present invention, said anti-heart failure agent is an ACE inhibitor, an angiotensin receptor blocker, an angiotensin-receptor neprilysin inhibitor, a beta adrenergic receptor blocker, a calcium channel blocker, or a vasodilator.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases "concurrent administration," "co-administration," "simultaneous administration," and "administered simultaneously" mean that the compounds are administered in combination. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition (e.g., NASH, heart failure or diabetes).

Given the NASH/NAFLD activity of the compounds of this invention, they may be co-administered with other agents for the treatment of non-alcoholic steatohepatitis (NASH) and/or non-alcoholic fatty liver disease (NAFLD) and associated disease/conditions, such as Orlistat, TZDs and other insulin-sensitizing agents, FGF21 analogs, Metformin, Omega-3-acid ethyl esters (e.g. Lovaza), Fibrates, HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)), Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), Phentermine, Topiramate, GLP-1 receptor agonists, GIP receptor agonists, dual GLP-1 receptor/glucagon receptor agonists (i.e., OPK88003, MED10382, JNJ-64565111, NN9277, BI 456906), dual GLP-1 receprtor/GIP receptor agonists (i.e., Tirzepatide (LY3298176), NN9423), Angiotensin-receptor blockers an acetyl-CoA carboxylase (ACC) inhibitor, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a PNPLA3 inhibitor, a an FGF21 analog, an FGF19 analog, a PPAR agonist, a FXR agonist, an AMPK activator, an SCD1 inhibitor or an MPO inhibitor.

Exemplary GLP-1 receptor agonists include liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, and those described in PCT/IB2019/054867 filed Jun. 11, 2019 including the following:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salts thereof.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid; and firsocostat (GS-0976) and pharmaceutically acceptable salts thereof.

Exemplary FXR Agonists include tropifexor (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid); cilofexor (GS-9674); obeticholic acid; LY2562175; Met409; TERN-101; and EDP-305 and pharmaceutically acceptable salts thereof.

Exemplary DGAT2 inhibitors include (S)-2-(5-((3-ethoxypyridin-2-yl)oxy)pyridin-3-yl)-N-(tetrahydrofuran-3-yl)pyrimidine-5-carboxamide;

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt thereof.

Exemplary KHK inhibitors include [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid and pharmaceutically acceptable salts thereof.

Given the anti-diabetic activity of the compounds of this invention they may be co-administered with other anti-diabetic agents. Suitable anti-diabetic agents include insulin, metformin, GLP-1 receptor agonists (described herein above), an acetyl-CoA carboxylase (ACC) inhibitor (described herein above), SGLT2 inhibitors (described herein above), monoacylglycerol O-acyltransferase inhibitors, phosphodiesterase (PDE)-10 inhibitors, AMPK activators, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, α-amylase inhibitors (e.g., tendamistat, trestatin and AL-3688), an α-glucoside hydrolase inhibitor (e.g., acarbose), α-glucosidase inhibitors (e.g., adiposine, camiglibose, emiglitate, miglitol, voglibose, pradimicin-Q, and salbostatin), PPARγ agonists (e.g., balaglitazone, ciglitazone, darglitazone, englitazone, isaglitazone, pioglitazone and rosiglitazone), PPAR α/γ agonists (e.g., CLX-0940, GW-1536, GW-1929, GW-2433, KRP-297, L-796449, LR-90, MK-0767 and SB-219994), protein tyrosine phosphatase-1B (PTP-1B) inhibitors (e.g., trodusquemine, hyrtiosal extract, and compounds disclosed by Zhang, S., et al., Drug Discovery Today, 12(9/10), 373-381 (2007)), SIRT-1 activators (e.g., resveratrol, GSK2245840 or GSK184072), dipeptidyl peptidease IV (DPP-IV) inhibitors (e.g., those in WO2005116014, sitagliptin, vildagliptin, alogliptin, dutogliptin, linagliptin and saxagliptin), insulin secreatagogues, a fatty acid oxidation inhibitors, A2 antagonists, c-jun amino-terminal kinase (JNK) inhibitors, glucokinase activators (GKa) such as those described in WO2010103437, WO201010343f8, WO2010013161, WO2007122482, TTP-399, TTP-355, TTP-547, AZD1656, ARRY403, MK-0599, TAK-329, AZD5658 or GKM-001, insulin, insulin mimetics, glycogen phosphorylase inhibitors (e.g. GSK1362885), VPAC2 receptor agonists, glucagon receptor modulators such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611.

Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKC$\alpha$, PKC$\beta$, PKC$\gamma$), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Given the anti-heart failure activity of the compounds of the present invention they may be co-administered with other anti-heart failure agents such as ACE inhibitors (e.g. captopril, enalapril, fosinopril, Lisinopril, perindopril, quinapril, Ramipril, trandolapril), Angiotensin II receptor blockers (e.g., Candesartan, Losartan, Valsartan), Angiotensin-receptor neprilysin inhibitors (sacubitril/valsartan), If channel blocker Ivabradine, Beta-Adrenergic blocking agents (e.g., bisoprolol, metoprolol succinate, carvedilol), Aldosterone antagonists (e.g., spironolactone, eplerenone), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of the present invention may also be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/All antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug-eluting stents, stem cell therapy and medical devices such as implanted pacemakers, defibrillators, or cardiac resynchronization therapy.

Particularly when provided as a single dosage unit, the potential exists for a chemical interaction between the combined active ingredients. For this reason, when a Formula I compound and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods.

The Formula I compounds of this invention, their prodrugs and the salts of such compounds and prodrugs are all adapted to therapeutic use as agents that inhibit BCKDK in mammals, particularly humans and thus are useful for the treatment of the various conditions (e.g., those described herein) in which such action is implicated.

The disease/conditions that can be treated in accordance with the present invention include, but are not limited to NASH/NAFLD, diabetes, and heart failure and associated disease/conditions.

In particular, inhibition of BCKDK is associated with NASH/NAFLD and associated disease/conditions because Increased BCAA levels were observed in human NASH samples (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human nonalcoholic fatty liver disease. Amino Acids 2015, 47:603-15). Reduced levels of PPM1K mRNA and increased BCKDK protein levels were also observed in human NASH (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human nonalcoholic fatty liver disease. Amino Acids 2015, 47:603-15). Treatment of obese mice or rats with a BCKDK inhibitor reduced hepatic steatosis and triglyceride content, and overexpression of PPM1K in rats reduced hepatic triglyceride content (White P J, McGarrah R W, Grimsrud P A, Tso S C, Yang W H, Haldeman J M, Grenier-Larouche T, An J, Lapworth A L, Astapova I, Hannou S A, George T, Arlotto M, Olson L B, Lai M, Zhang G F, Ilkayeva O, Herman M A, Wynn R M, Chuang D T, Newgard C B: The BCKDH Kinase and Phosphatase Integrate BCAA and Lipid Metabolism via Regulation of ATP-Citrate Lyase. Cell Metab 2018, 27(6), 1281-1293). Further, regulatory authority recognized conditional approval for Phase III studies in NASH is based on histological surrogate markers obtained by liver biopsy. These generally accepted surrogates are i) resolution of NASH without worsening of fibrosis (i.e. a numerical increase in fibrosis stage); ii) a one or more stage reduction in fibrosis without worsening of NASH. Details may be found in: Ratziu, A critical review of endpoints for non-cirrhotic NASH therapeutic trials, Journal of Hepatology, 2018, 68. 353-361, and references therein.

Accordingly, given the positive correlation between activation of BCKDK with the development of NASH/NAFLD and associated disease/conditions, Formula I compounds of this invention, their prodrugs and the salts of such compounds and prodrugs, by virtue of their pharmacologic action, are useful for the prevention, arrestment and/or regression of fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma In addition, increased BCKDK is associated with heart failure and associated disease/conditions because an increase in BCKA have been observed in hearts from patients with heart failure. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

In heart failure, the regulatory phosphatase that activates BCKDH (PPM1K) is downregulated, and BCKDK is upregulated; thus BCAA catabolism is likely impaired in heart failure. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

Both BCKDH and BCKDK are expressed ubiquitously; however, the regulatory phosphatase PPM1K, which dephosphorylates BCKDH, is expressed most highly in cardiac tissue. Mice lacking PPM1K develop aging-induced heart failure and have worsened heart function when subjected to a transverse aortic constriction (TAC) heart failure model. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

Use of an inhibitor of BCKDK improved cardiac function in three different preclinical heart failure models (TAC, left anterior descending artery ligation/myocardial infarct, and ischemia/reperfusion). (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49; Wang W, Zhang F, Xia Y, Zhao S, Yan W, Wang H, Lee Y, Li C, Zhang L, Lian K, Gao E, Cheng H, Tao L: Defective branched chain amino acid catabolism contributes to cardiac dysfunction and remodeling following myocardial infarction. Am J Physiol Heart Circ Physiol 2016, 311:H1160-H9; Li T, Zhang Z, Kolwicz S C, Jr., Abell L, Roe N D, Kim M, Zhou B, Cao Y, Ritterhoff J, Gu H, Raftery D, Sun H, Tian R: Defective Branched-Chain Amino Acid Catabolism Disrupts Glucose Metabolism and Sensitizes the Heart to Ischemia-Reperfusion Injury. Cell Metab 2017, 25:374-85.)

Therefore, inhibiting BCKDK in cardiac or peripheral tissue should demonstrate benefit for metabolic disease and cardiac function.

Accordingly, given the positive correlation between activation of BCKDK with the development of heart failure and associated disease/conditions, Formula I compounds of this invention, their prodrugs and the salts of such compounds and prodrugs, by virtue of their pharmacologic action, are useful for the prevention, arrestment and/or regression of heart failure, congestive heart failure, unstable angina, peripheral arterial disease, pulmonary hypertension, vasculitis or where the mammal has experienced myocardial infarction (secondary prevention ($2^{nd}$ myocardial infarction)).

In addition, increased BCKDK is associated with diabetes and associated disease/conditions because plasma BCAA are upregulated in patients with increased fasting glucose levels, and a one Standard Deviation increase in BCKA concentrations in plasma increases the likelihood of developing diabetes by over 50%. (Wang T J, Larson M G, Vasan R S, Cheng S, Rhee E P, McCabe E, Lewis G D, Fox C S, Jacques P F, Fernandez C, O'Donnell C J, Carr S A, Mootha V K, Florez J C, Souza A, Melander O, Clish C B, Gerszten R E: Metabolite profiles and the risk of developing diabetes. Nat Med 2011, 17:448-53; Newgard C B, An J, Bain J R, Muehlbauer M J, Stevens R D, Lien L F, Haqq A M, Shah S H, Arlotto M, Slentz C A, Rochon J, Gallup D, Ilkayeva O, Wenner B R, Yancy W S, Jr., Eisenson H, Musante G, Surwit R S, Millington D S, Butler M D, Svetkey L P: A branched-chain amino acid-related metabolic signature that differentiates obese and lean humans and contributes to insulin resistance. Cell Metab 2009, 9:311-26; Menni C, Fauman E, Erte I, Perry J R, Kastenmuller G, Shin S Y, Petersen A K, Hyde C, Psatha M, Ward K J, Yuan W, Milburn M, Palmer C N, Frayling™, Trimmer J, Bell J T, Gieger C, Mohney R P, Brosnan M J, Suhre K, Soranzo N, Spector T D: Biomarkers for type 2 diabetes and impaired fasting glucose using a nontargeted metabolomics approach. Diabetes 2013, 62:4270-6.)

Genetic analyses suggest that loss of function mutations in the PPM1K locus increase BCAA/BCKA levels and are associated with development of type 2 diabetes. (Lotta L A, Scott R A, Sharp S J, Burgess S, Luan J, Tillin T, Schmidt A F, Imamura F, Stewart I D, Perry J R, Marney L, Koulman A, Karoly E D, Forouhi N G, Sjogren R J, Naslund E, Zierath J R, Krook A, Savage D B, Griffin J L, Chaturvedi N, Hingorani A D, Khaw K T, Barroso I, McCarthy M I, O'Rahilly S, Wareham N J, Langenberg C: Genetic Predisposition to an Impaired Metabolism of the Branched-Chain Amino Acids and Risk of Type 2 Diabetes: A Mendelian Randomisation Analysis. PLoS Med 2016, 13:e1002179.)

Treatment of diabetic, obese mice or rats with a BCKDK inhibitor improved fasting glycemia, glycemia in a glucose tolerance test, reduced insulin levels, and improved insulin sensitivity. Overexpression of PPM1K in rats also improved glycemia and reduced insulin levels. (White P J, McGarrah R W, Grimsrud P A, Tso S C, Yang W H, Haldeman J M, Grenier-Larouche T, An J, Lapworth A L, Astapova I, Hannou S A, George T, Arlotto M, Olson L B, Lai M, Zhang G F, Ilkayeva O, Herman M A, Wynn R M, Chuang D T, Newgard C B: The BCKDH Kinase and Phosphatase Integrate BCAA and Lipid Metabolism via Regulation of ATP-Citrate Lyase. Cell Metab 2018.)

Accordingly, given the positive correlation between BCKDK and the development of diabetes and associated disease/conditions, Formula I compounds of this invention, their prodrugs and the salts of such compounds and prodrugs, by virtue of their pharmacologic action, are useful for the prevention, arrestment and/or regression of Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertrygliceridemia, insulin resistance, impaired glucose metabolism, skin and connective tissue disorders, foot ulcerations and ulcerative colitis, endothelial dysfunction and impaired vascular compliance, and hyper apo B lipoproteinemia.

Administration of the compounds of this invention can be via any method which delivers a compound of this invention systemically and/or locally. These methods include oral routes, parenteral, intraduodenal routes, buccal, intranasal etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the compounds herein may be in the range 1 mg to 5000 mg depending, of course, on the mode of and frequency of administration, the disease state, and the age and condition of the patient, etc. An oral daily dose is in the range of 3 mg to 2000 mg may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the compound of the present invention. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjunction with the Formula I compounds is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula I for use as a medicament (such as a unit dosage tablet or unit dosage capsule). In another embodiment, the present invention comprises the use of a compound of Formula I for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multi-particulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about C.sub.8 to C.sub.10) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 μg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(RO-102) (15.8%), sodium starch (7%), sodium lauryl sulfate (2%) and magnesium stearate (1%).

The HPMCAS polymers are available in low, medium and high grades as Aqoa.sup.®-LF, Aqoat.sup.®-MF and Aqoat.sup.®-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about 0.001 to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences,* 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

The compounds and intermediates described below were named using the naming convention provided with ACD/ChemSketch 2017.2.1, File Version N40E41, Build 96719 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. "Room temperature" or "ambient temperature" means a temperature between 15° C. and 25° C., and "UPLC" refers to ultra-performance liquid chromatography, Hydrogenation may be performed in a Parr shaker under pressurized hydrogen gas, or in a Thales-nano H-Cube flow hydrogenation apparatus at full hydrogen and a flow rate between 1-2 mL/min at specified temperature.

HPLC, UPLC, LCMS, and SFC retention times were measured using the methods noted in the procedures.

Caution: Tetrazoles are generally considered a high energy functional group and care should be taken in the synthesis and handling of tetrazole containing molecules.

Example 1

5-(4-Bromo-3-methylthiophen-2-yl)-1H-tetrazole (1)

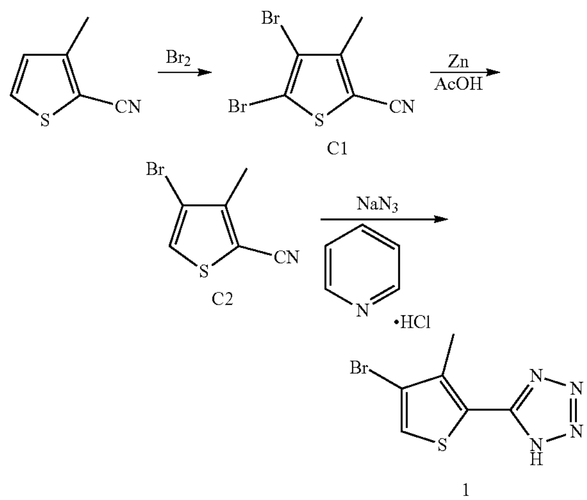

C1

C2

1

Step 1. Synthesis of 4,5-dibromo-3-methylthiophene-2-carbonitrile (C1)

Bromine (9.98 mL, 195 mmol) was added to a 0° C. solution of 3-methylthiophene-2-carbonitrile (4.0 g, 32 mmol) in N,N-dimethylformamide (16 mL), and the reaction mixture was heated to 60° C. for 16 hours. After addition of saturated aqueous sodium sulfite solution (80 mL), the mixture was stirred at 15° C. for 1 hour; the resulting solid was collected via filtration and washed with water to provide C1 as an off-white solid. Yield: 7.78 g, 27.7 mmol, 87%. $^1H$ NMR (400 MHz, chloroform-d) δ 2.46 (s, 3H).

Step 2. Synthesis of 4-bromo-3-methylthiophene-2-carbonitrile (C2)

A mixture of C1 (5.0 g, 18 mmol) and zinc (2.33 g, 35.6 mmol) in acetic acid (50 mL) and water (12.5 mL) was stirred at 105° C. for 1 hour. After the reaction mixture had cooled, it was concentrated in vacuo, and the residue was dissolved in ethyl acetate (50 mL) and washed sequentially with water (3×50 mL) and dilute aqueous sodium carbonate solution (3×50 mL). Removal of solvents under reduced pressure provided C2 as a brown solid, which was used in the following step without additional purification. Yield: 2.40 g, 11.9 mmol, 66%. $^{1}$H NMR (400 MHz, chloroform-d) δ 7.47 (s, 1H), 2.42 (s, 3H).

Step 3. Synthesis of 5-(4-bromo-3-methylthiophen-2-yl)-1H-tetrazole (1)

Sodium azide (927 mg, 14.3 mmol) and pyridine hydrochloride (1.37 g, 11.9 mmol) were added to a solution of C2 (2.40 g, 11.9 mmol) in N,N-dimethylformamide (50 mL). The reaction mixture was then heated to 110° C. for 16 hours, whereupon it was treated with water (50 mL) and extracted with a mixture of ethyl acetate and tetrahydrofuran (1:1, 3×50 mL). The combined organic layers were concentrated in vacuo and purified via reversed-phase HPLC (Column: Phenomenex Synergi Max-RP, 10 μm; Mobile phase A: 0.225% formic acid in water; Mobile phase B: acetonitrile; Gradient: 20% to 40% B), affording 1 as a white solid. Yield: 961 mg, 3.92 mmol, 33%. LCMS m/z 245.0 (bromine isotope pattern observed) $[M+H]^+$. $^{1}$H NMR (400 MHz, methanol-$d_4$) δ 7.71 (s, 1H), 2.55 (s, 3H).

Example 2

5-(5-Fluoro-3-methylthiophen-2-yl)-1H-tetrazole (2)

Step 1. Synthesis of 5-(3-methylthiophen-2-yl)-1H-tetrazole (C3)

To a solution of 3-methylthiophene-2-carbonitrile (1.00 g, 8.12 mmol) in N,N-dimethylformamide (30 mL) was added sodium azide (0.633 g, 9.74 mmol), followed by pyridine hydrochloride (0.938 g, 8.12 mmol). The reaction mixture was stirred at 100° C. for 16 hours, whereupon it was cooled to room temperature, treated with aqueous sodium hydroxide solution (4.85 M; 10 mL, 48 mmol), and allowed to stir for 30 minutes. The resulting mixture was vigorously stirred with diethyl ether (100 mL), and the aqueous layer was washed with diethyl ether (2×100 mL); these organic layers were discarded. The aqueous layer was then acidified to pH 1 by drop-wise addition of hydrochloric acid (6 M; approximately 35 mL), and extracted with diethyl ether (3×100 mL). These organic layers were combined and extracted with saturated aqueous sodium bicarbonate solution (150 mL); the resulting aqueous layer was washed with diethyl ether (2×100 mL), and again these organic layers were discarded. The aqueous layer was acidified to pH 1 by addition of hydrochloric acid (6 M; approximately 100 mL) and extracted with diethyl ether (3×100 mL). These combined organic layers were dried over magnesium sulfate, filtered, and concentrated in vacuo to provide C3 as a yellow solid. Yield: 557 mg, 3.35 mmol, 41%. LCMS m/z 167.0 $[M+H]^+$. $^{1}$H NMR (400 MHz, methanol-$d_4$) δ 7.60 (d, J=5.1 Hz, 1H), 7.07 (d, J=5.1 Hz, 1H), 2.55 (s, 3H).

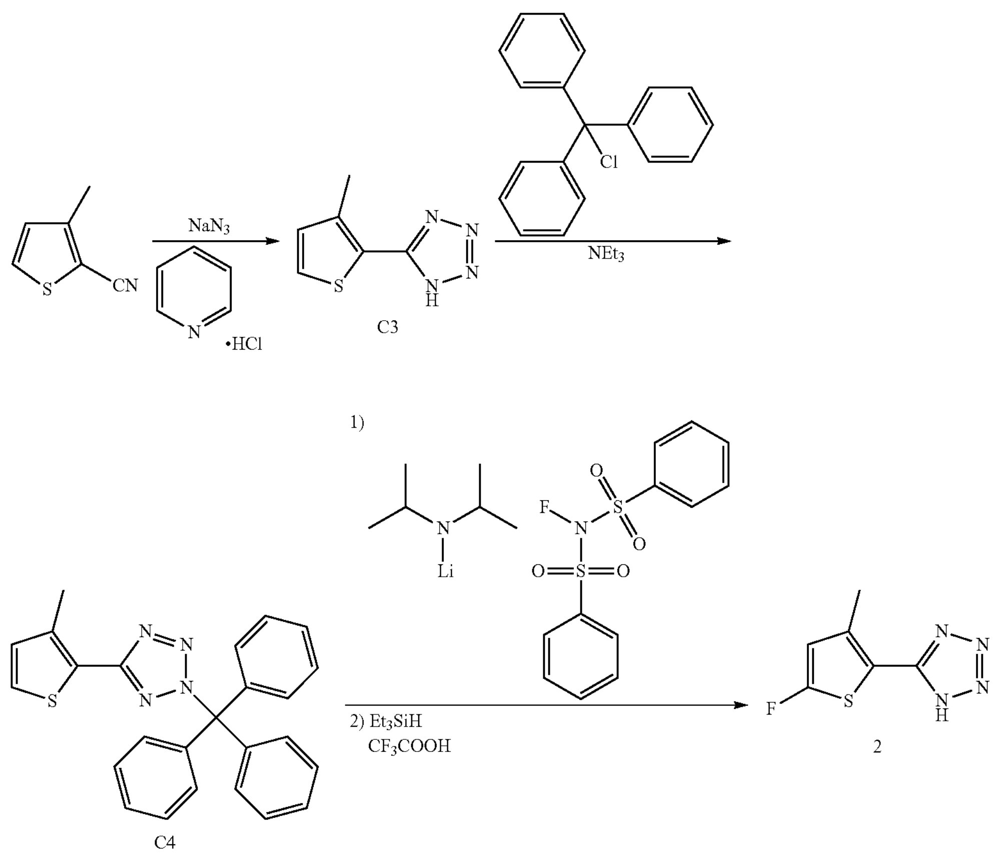

C3

C4

2

Step 2. Synthesis of 5-(3-methylthiophen-2-yl)-2-trityl-2H-tetrazole (C4)

Triethylamine (0.171 mL, 1.23 mmol) and triphenylmethyl chloride (0.189 g, 0.678 mmol) were added to a solution of C3 (0.102 g, 0.614 mmol) in dichloromethane (2 mL), and the reaction mixture was allowed to stir at room temperature for 16 hours. It was then diluted with dichloromethane (100 mL) and sequentially washed with water (3 20×100 mL) and saturated aqueous sodium chloride solution (150 mL), dried over sodium sulfate, filtered, and concentrated in vacuo, providing C4 as a white solid. This material was not entirely pure by $^1$H NMR analysis. Yield: 260 mg, assumed quantitative. $^1$H NMR (400 MHz, chloroform-d), characteristic peaks: δ 6.93 (d, J=5.0 Hz, 1H), 2.49 (s, 3H).

Step 3. Synthesis of 5-(5-fluoro-3-methylthiophen-2-yl)-1H-tetrazole (2)

A solution of lithium diisopropylamide (2.0 M; 0.636 mL, 1.27 mmol) was added in a drop-wise manner to a −78° C. solution of C4 (from the previous step; 260 mg, 0.614 mmol) in tetrahydrofuran (5 mL), at a rate such that the internal reaction temperature did not rise above −76° C. After completion of the addition, the reaction mixture was allowed to stir at −78° C. for 5 hours, whereupon a solution of N-fluoro-N-(phenylsulfonyl)benzenesulfonamide (401 mg, 1.27 mmol) in tetrahydrofuran (2 mL) was added drop-wise. Stirring was continued for 30 minutes at −78° C., and then the reaction mixture was allowed to warm to room temperature over 16 hours. Water was added, and the resulting mixture was extracted twice with ethyl acetate; the combined organic layers were washed with saturated aqueous sodium chloride solution, dried over sodium sulfate, filtered, and concentrated in vacuo. In order to remove the protecting group, the residue was dissolved in dichloromethane (5 mL) and treated with trifluoroacetic acid (0.490 mL, 6.36 mmol) followed by triethylsilane (0.508 mL, 3.18 mmol). After the reaction mixture had stirred at room temperature for 1 hour, it was diluted with aqueous sodium bicarbonate solution and washed three times with dichloromethane. The organic layers were discarded, and the aqueous layer was adjusted to pH 1 by addition of 1 M hydrochloric acid. The aqueous layer was then extracted three times with dichloromethane, and these organic layers were combined, dried over sodium sulfate, filtered, and concentrated in vacuo. Purification via reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 5% to 95% B) provided 2 as a solid. Yield: 6.4 mg, 34.7 μmol, 6%. LCMS m/z 185.1 [M+H]$^+$. $^1$H NMR (400 MHz, chloroform-d) 66.43 (d, J=1.8 Hz, 1H), 2.53 (s, 3H).

Examples 3 and 4

5-(4-Chloro-3-ethylthiophen-2-yl)-1H-tetrazole, ammonium salt (3) and 5-(4-Bromo-3-ethylthiophen-2-yl)-1H-tetrazole, ammonium salt (4)

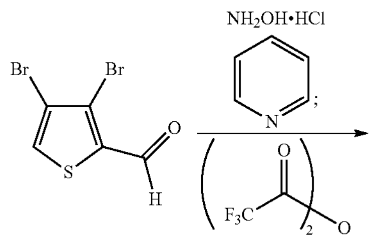

-continued

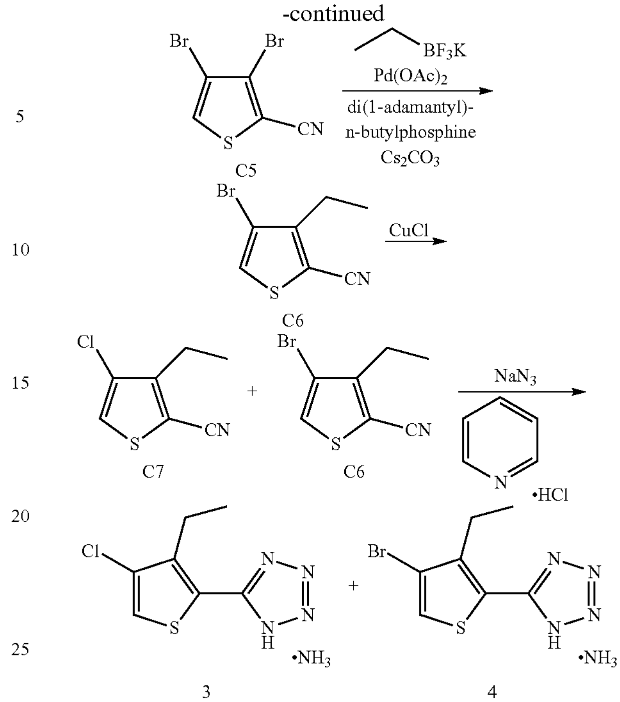

C5

C6

C7 + C6

3 + 4

Step 1. Synthesis of 3,4-dibromothiophene-2-carbonitrile (C5)

Pyridine (5.25 mL, 64.9 mmol) was added over 20 minutes, in a drop-wise manner, to a mixture of 3,4-dibromothiophene-2-carbaldehyde (2.93 g, 10.9 mmol) and hydroxylamine hydrochloride (0.830 g, 11.9 mmol) in acetonitrile (27 mL). The reaction mixture was allowed to stir at room temperature for 1.5 hours, whereupon trifluoroacetic anhydride (3.77 mL, 26.7 mmol) was added in a drop-wise manner over 30 minutes. After a further 2.5 hours at room temperature, the reaction mixture was poured into a mixture of hydrochloric acid (0.05 M; 200 mL) and ethyl acetate (150 mL). The aqueous layer was extracted with ethyl acetate (2×100 mL), and the combined organic layers were dried over sodium sulfate, filtered, and concentrated in vacuo. Silica gel chromatography (Gradient: 0% to 40% ethyl acetate in heptane) provided C5 as a light yellow solid. Yield: 2.34 g, 8.77 mmol, 80%. $^1$H NMR (400 MHz, chloroform-d) δ 7.58 (s, 1H).

Step 2. Synthesis of 4-bromo-3-ethylthiophene-2-carbonitrile (C6)

A reaction vessel containing C5 (1.00 g, 3.75 mmol), potassium ethyltrifluoroborate (0.509 g, 3.74 mmol), palladium(II) acetate (84.1 mg, 0.375 mmol), di(1-adamantyl)-n-butylphosphine (0.161 g, 0.449 mmol), and cesium carbonate (3.66 g, 11.2 mmol) in toluene (11 mL) and water (1 mL) was evacuated and charged with nitrogen. This evacuation cycle was repeated twice, and then the reaction mixture was heated to 100° C. for 24 hours. After cooling to room temperature, it was partitioned between dichloromethane (100 mL) and water (150 mL), and the aqueous layer was extracted with dichloromethane (2×100 mL). The combined organic layers were dried over sodium sulfate, filtered, concentrated in vacuo, and purified via silica gel chromatography (Gradient: 0% to 30% ethyl acetate in heptane). A light yellow, oily material was isolated, containing C6 along with minor impurities; this material was advanced to the following step. Yield: 236 mg, 1.09 mmol, 29%. $^{1}H$ NMR (400 MHz, chloroform-d), product peaks only: δ 7.46 (s, 1H), 2.84 (q, J=7.6 Hz, 2H), 1.25 (t, J=7.6 Hz, 3H).

Step 3. Synthesis of 4-chloro-3-ethylthiophene-2-carbonitrile (C7)

To a solution of C6 (0.235 g, 1.09 mmol) in N,N-dimethylformamide (54 mL) was added copper(I) chloride (0.215 g, 2.17 mmol), and the reaction mixture was heated to 140° C. for 16 hours. After it had cooled to room temperature, the reaction mixture was partitioned between saturated aqueous ammonium chloride solution (100 mL) and diethyl ether (100 mL). The organic layer was washed sequentially with saturated aqueous ammonium chloride solution (2×100 mL), water (3×100 mL), and saturated aqueous sodium chloride solution (200 mL), then dried over sodium sulfate, filtered, and concentrated in vacuo. Chromatography on silica gel (Gradient: 0% to 15% ethyl acetate in heptane) provided a colorless oil (166 mg); GCMS analysis indicated that both starting material C6 {GCMS m/z 215 (bromine isotope pattern observed) [$M^+$]} and product C7 {GCMS m/z 171 (chlorine isotope pattern observed) [$M^+$]} were present. This material was advanced directly into the following step.

Step 4. Synthesis of 5-(4-chloro-3-ethylthiophen-2-yl)-1H-tetrazole, ammonium salt (3) and 5-(4-bromo-3-ethylthiophen-2-yl)-1H-tetrazole, ammonium salt (4)

Sodium azide (88.0 mg, 1.35 mmol) was added to a solution of C7 and C6 (from the previous step: 0.166 g, <1.09 mmol) in N,N-dimethylformamide (3.6 mL), followed by addition of pyridine hydrochloride (134 mg, 1.16 mmol). The reaction mixture was stirred at 100° C. for 16 hours, whereupon it was cooled to room temperature and treated with aqueous sodium hydroxide solution (4.85 M; 10 mL, 48 mmol). After the resulting mixture had been stirred for 30 minutes, it was diluted with diethyl ether (100 mL) and vigorously stirred for 5 minutes. The aqueous layer was washed with diethyl ether (2×100 mL); the organic layers were discarded, and the aqueous layer was acidified to pH 1 by drop-wise addition of hydrochloric acid (6 M; approximately 35 mL). It was then extracted with diethyl ether (3×100 mL), and the combined organic layers were extracted with saturated aqueous sodium bicarbonate solution (150 mL). This basic aqueous layer was washed with diethyl ether (2×100 mL), acidified to pH 1 by addition of hydrochloric acid (6 M; approximately 100 mL), and extracted with diethyl ether (3×100 mL). These three organic layers were combined, dried over magnesium sulfate, filtered, and concentrated in vacuo to provide a light yellow solid (131 mg). The two components were separated using reversed-phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 5% to 20% B). Chloro product 3 was isolated as a solid. Yield: 20.3 mg, 87.6 μmol, 8% over 2 steps. LCMS m/z 215.2 (chlorine isotope pattern observed) $[M+H]^+$. $^{1}H$ NMR (600 MHz, DMSO-$d_6$) δ 7.87 (s, 1H), 2.99 (q, J=7.4 Hz, 3H), 1.14 (t, J=7.5 Hz, 5H).

Bromo product 4 was isolated as a white solid. Yield: 40.6 mg, 0.147 mmol, 13% over 2 steps. LCMS m/z 259.1 (bromine isotope pattern observed) $[M-H^+]$. $^{1}H$ NMR (400 MHz, DMSO-$d_6$) δ 7.62 (s, 1H), 7.20 (br s, 1H), 7.08 (br s, 1H), 6.95 br (s, 1H), 3.05 (q, J=7.4 Hz, 2H), 1.11 (t, J=7.4 Hz, 3H).

Example 5

5-[3-(Difluoromethyl)thiophen-2-yl]-1H-tetrazole (5)

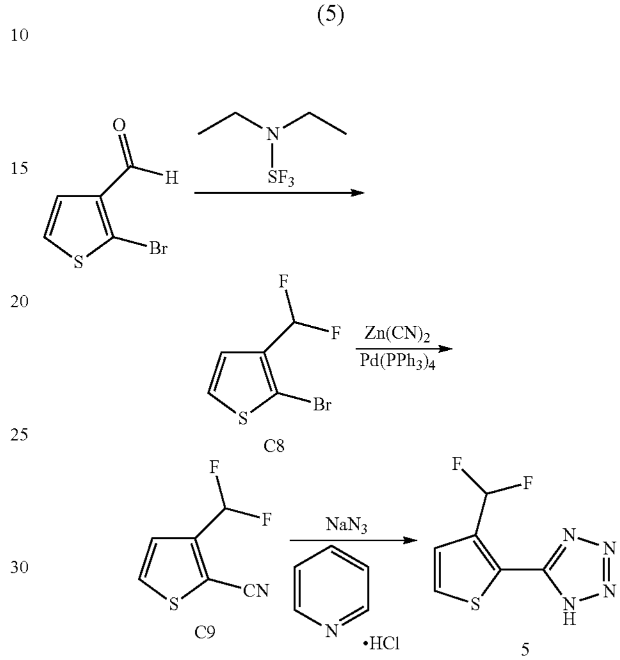

C8

C9

5

Step 1. Synthesis of 2-bromo-3-(difluoromethyl)thiophene (C8)

A solution of 2-bromothiophene-3-carbaldehyde (0.95 g, 5.0 mmol) in dichloromethane (17 mL) was cooled to 0° C., and then treated in a drop-wise manner with (diethylamino) sulfur trifluoride (2.0 mL, 15 mmol). The reaction mixture was allowed to warm to room temperature and stir tor 16 hours, whereupon it was carefully treated portion-wise with saturated aqueous sodium bicarbonate solution (300 mL). The aqueous layer was extracted with dichloromethane (3×100 mL), and the combined organic layers were dried over sodium sulfate, filtered, and concentrated under reduced pressure to provide C8 as an oily orange solid (1.04 g). A portion of this material was used directly in the following step. $^{1}H$ NMR (400 MHz, chloroform-d) δ 7.33 (d, J=5.8 Hz, 1H), 7.13 (d, J=5.7 Hz, 1H), 6.68 (t, $J_{HF}$=54.8 Hz, 1H).

Step 2. Synthesis of 3-(difluoromethyl)thiophene-2-carbonitrile (C9)

Tetrakis(triphenylphosphine)palladium(0) (542 mg, 0.469 mmol) and zinc cyanide (0.551 g, 4.69 mmol) were added to a solution of C8 (from the previous step; 0.50 g, 52.4 mmol) in N,N-dimethylformamide (17 mL). The reaction vial was sealed and heated to 117° C. for 16 hours, whereupon it was cooled to room temperature; GCMS analysis of the reaction mixture at this point showed the presence of product: GCMS m/z 159.0 [M*]. The reaction mixture was diluted with saturated aqueous sodium bicarbonate solution (100 mL)

and extracted with diethyl ether (3×100 mL). The combined organic layers were washed sequentially with water (3×150 mL) and with saturated aqueous sodium chloride solution (150 mL), dried over sodium sulfate, filtered, and concentrated in vacuo. Chromatography on silica gel (Gradient: 0% to 40% ethyl acetate in heptane) afforded C9 as an oily, light yellow residue. Yield: 115 mg, 0.723 mmol, 30% over 2 steps. $^1$H NMR (400 MHz, chloroform-d) δ 7.66 (d, J=5.2 Hz, 1H), 7.32 (d, J=5.2 Hz, 1H), 6.84 (t, $J_{HF}$=54.6 Hz, 1H).

Step 3. Synthesis of 5-[3-(difluoromethyl)thiophen-2-yl]-1H-tetrazole (5)

Sodium azide (56.4 mg, 0.867 mmol) and pyridine hydrochloride (83.5 mg, 0.723 mmol) were added to a solution of C9 (115 mg, 0.723 mmol) in N,N-dimethylformamide (3 mL), and the reaction mixture was heated to 100° C. for 24 hours. After it had cooled to room temperature, the reaction mixture was treated with aqueous sodium hydroxide solution (4.85 M; 5 mL) and allowed to stir for 30 minutes. It was then diluted with dichloromethane (50 mL) and stirred vigorously for 5 minutes, whereupon the layers were separated and the aqueous layer was washed with dichloromethane (2×50 mL). The dichloromethane layers were discarded, and the aqueous layer was acidified to pH 1 by drop-wise addition of concentrated hydrochloric acid, and then extracted with dichloromethane (3×50 mL). These organic layers were combined, dried over magnesium sulfate, filtered, and concentrated in vacuo; the following day, an orange solid was present, which was triturated with dichloromethane (2 mL) and then further washed with dichloromethane (2×3 mL) to afford 5 as a white solid (15.7 mg). The filtrate was concentrated under reduced pressure to provide additional 5 as a white solid (72 mg). Yield: 87.7 mg, 0.434 mmol, 60%. LCMS m/z 201.2 [M−H$^+$] $^1$H NMR (400 MHz, DMSO-$d_6$) δ 7.95 (d, J=5.3 Hz, 1H), 7.55 (t, $J_{HF}$=54.7 Hz, 1H), 7.47 (d, J=5.3 Hz, 1H).

Example 6

5-[5-Chloro-3-(difluoromethyl)thiophen-2-yl]-1H-tetrazole (6)

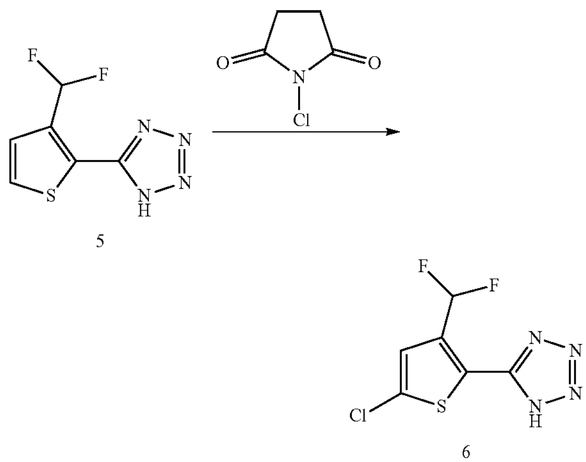

5

6

To a solution of 5 (72 mg, 0.36 mmol) in N,N-dimethylformamide (0.36 mL) was added N-chlorosuccinimide (72.0 mg, 0.539 mmol). The reaction mixture was heated to 50° C. for 16 hours, whereupon it was diluted with aqueous sodium hydroxide solution (1 M; 10 mL) and washed with ethyl acetate (2×10 mL). The aqueous layer was then acidified to pH 1 with hydrochloric acid (1 M; 15 mL) and extracted with dichloromethane (2×10 mL); these dichloromethane layers were combined, dried over sodium sulfate, filtered, and concentrated in vacuo. The residue was dissolved in dichloromethane (25 mL), treated with saturated aqueous sodium bicarbonate solution (50 mL), and stirred for 10 minutes, whereupon the aqueous layer was washed with dichloromethane (3×25 mL). It was then acidified to pH 1 by addition of hydrochloric acid (3 M; approximately 10 mL), and extracted with dichloromethane (3×25 mL). These three organic layers were combined, dried over sodium sulfate, filtered, concentrated under reduced pressure, and subjected to silica gel chromatography (Gradient: 0% to 20% methanol in dichloromethane). The isolated material was triturated with dichloromethane to afford 6 as a white solid. Yield: 31 mg, 0.13 mmol, 36%. LCMS m/z 235.1 (chlorine isotope pattern observed) [M−H$^+$]. $^1$H NMR (400 MHz, DMSO-$d_6$) δ 7.57 (s, 1H), 7.50 (t, $J_{HF}$=54.4 Hz, 1H).

Example 7

5-(3-Chlorothiophen-2-yl-1H-tetrazole (7)

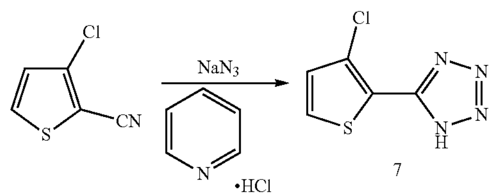

7

Sodium azide (0.543 g, 8.35 mmol) and pyridine hydrochloride (0.805 g, 6.97 mmol) were added to a solution of 3-chlorothiophene-2-carbonitrile (1.00 g, 6.96 mmol) in N,N-dimethylformamide (26 mL), and the reaction mixture was heated to 100° C. for 16 hours. After it had cooled to room temperature, the reaction mixture was treated with aqueous sodium hydroxide solution (4.85 M; 10 mL) and allowed to stir for 30 minutes. It was then diluted with dichloromethane (100 mL) and stirred vigorously for 5 minutes, whereupon the layers were separated and the aqueous layer was washed with dichloromethane (2×100 mL). The dichloromethane layers were discarded, and the aqueous layer was acidified to pH 1 by drop-wise addition of concentrated hydrochloric acid, and then extracted with dichloromethane (3×100 mL). These organic layers were combined, dried over magnesium sulfate, filtered, and concentrated in vacuo; the resulting solid was triturated with dichloromethane (10 mL) to provide 7 as a white solid. Yield: 536 mg, 2.87 mmol, 41%. LCMS m/z 185.1 (chlorine isotope pattern observed) [M−H$^+$]. $^1$H NMR (400 MHz, DMSO-$d_6$) δ 7.98 (d, J=5.4 Hz, 1H), 7.31 (d, J=5.3 Hz, 1H).

Example 8

5-(5-Bromo-3-chlorothiophen-2-yl)-1H-tetrazole (8)

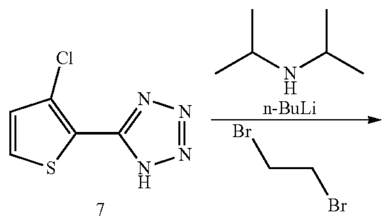

7

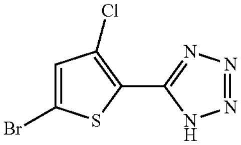

8 n-Butyllithium (2.5 M; 0.429 mL, 1.07 mmol) was added to a −78° C. solution of diisopropylamine (0.108 g, 1.07 mmol) in tetrahydrofuran (3.0 mL). After the addition had been completed, the reaction mixture was stirred for 1 hour, warmed to 0° C., stirred for 30 minutes, and then cooled to −78° C. A solution of 7 (0.100 g, 0.536 mmol) in tetrahydrofuran (1.0 mL) was added drop-wise, at a rate that maintained the internal reaction temperature below −70° C. throughout the addition. After the reaction mixture had been stirred for 1 hour at −78° C., a solution of 1,2-dibromoethane (92.8 μL, 1.08 mmol) in tetrahydrofuran (1.0 mL) was added, and stirring was continued for 1.5 hours at −78° C. The reaction mixture was then allowed to warm slowly to room temperature, whereupon it was poured into hydrochloric acid (1 M; 10 mL) and extracted with ethyl acetate (3×25 mL). The combined organic layers were dried over sodium sulfate, filtered, and concentrated in vacuo, providing an oily, light orange residue (98 mg). A portion of this material (30 mg) was purified via reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 15% to 55% B) to afford 8. Yield: 8.8 mg, 33 μmol, 20%. LCMS m/z 265.0 (bromo chloro isotope pattern observed) $[M+H]^+$. $^1H$ NMR (400 MHz, DMSO-$d_6$) δ 7.57 (s, 1H).

Example 9

5-(5-Chloro-3-methylthiophen-2-yl)-1H-tetrazole (9)

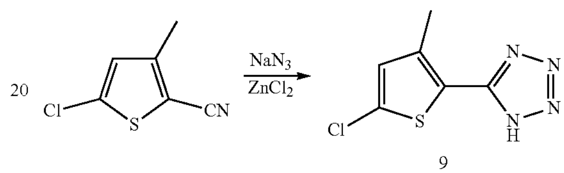

9

Sodium azide (421 mg, 6.47 mmol) and zinc chloride (735 mg, 5.39 mmol) were added to a solution of 5-chloro-3-methylthiophene-2-carbonitrile (850 mg, 5.39 mmol) in 1-propanol (14 mL), and the reaction mixture was heated at 95° C. overnight with vigorous stirring. It was then added to 1 M hydrochloric acid and stirred for 30 minutes, whereupon the mixture was extracted twice with ethyl acetate. The combined organic layers were washed with saturated aqueous sodium chloride solution, dried over sodium sulfate, filtered, and concentrated in vacuo. Silica gel chromatography (Gradient: 0% to 20% methanol in dichloromethane) provided purified material that was then triturated with dichloromethane and heptane, affording 9 as a white solid. Yield: 853 mg, 4.25 mmol, 79%. LCMS m/z 201.1 (chlorine isotope pattern observed) $[M+H]^+$. $^1H$ NMR (400 MHz, methanol-$d_4$) δ 6.99 (s, 1H), 2.51 (s, 3H).

Example 10

5-(5-Chloro-4-fluoro-3-methylthiophen-2-yl)-1H-tetrazole (10)

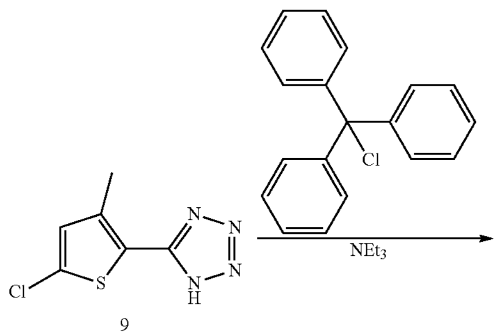

9

-continued

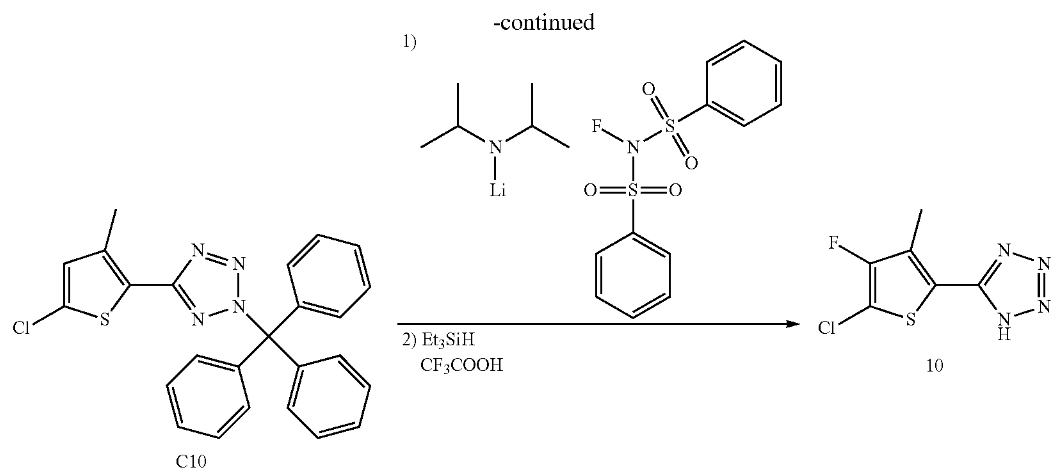

C10

10

Step 1. Synthesis of 5-(5-chloro-3-methylthiophen-2-yl)-2-trityl-2H-tetrazole (C10)

Triethylamine (0.139 mL, 0.997 mmol) and triphenylmethyl chloride (0.208 g, 0.746 mmol) were added to a solution of 9 (100 mg, 0.498 mmol) in dichloromethane (10 mL), and the reaction mixture was stirred at room temperature for 18 hours. It was then diluted with dichloromethane (100 mL) and washed sequentially with water (3×100 mL) and saturated aqueous sodium chloride solution (150 mL), dried over sodium sulfate, filtered, and concentrated in vacuo. Trituration of the residue with diethyl ether and heptane provided C10 as a white solid. Yield: 189 mg, 0.427 mmol, 86%. $^1$H NMR (400 MHz, chloroform-d) δ 7.40-7.29 (m, 9H), 7.17-7.12 (m, 6H), 6.77 (s, 1H), 2.44 (s, 3H).

Step 2. Synthesis of 5-(5-chloro-4-fluoro-3-methylthiophen-2-yl)-1H-tetrazole (10)

To a −78° C. solution of C10 (1.84 g, 4.14 mmol) in tetrahydrofuran (41 mL) was added lithium diisopropylamide (2.0 M solution in tetrahydrofuran/hexane/ethylbenzene; 4.14 mL, 8.28 mmol) in a drop-wise manner, at a rate such that the internal reaction temperature did not exceed −70° C. After the reaction mixture had been stirred at −78° C. for 2 hours, a solution of N-fluoro-N-(phenylsulfonyl)benzenesulfonamide (2.61 g, 8.28 mmol) in tetrahydrofuran (10 mL) was added drop-wise. Stirring was continued at −78° C. for 30 minutes, whereupon the reaction mixture was allowed to warm to room temperature over 16 hours. Water (50 mL) was then added, and the resulting mixture was extracted with ethyl ether (3×50 mL); the combined organic layers were washed with saturated aqueous sodium chloride solution (50 mL), dried over sodium sulfate, filtered, and concentrated in vacuo to provide an orange oil. This material was dissolved in dichloromethane (15 mL) and treated sequentially with triethylsilane (1.66 mL, 10.4 mmol) and trifluoroacetic acid (1.60 mL, 20.8 mmol). After this reaction mixture had been stirred at room temperature for 1.5 hours, it was concentrated under reduced pressure and the residue was partitioned between water and ethyl acetate. The aqueous layer was extracted twice with ethyl acetate, and the combined organic layers were washed with saturated aqueous sodium chloride solution, dried over sodium sulfate, filtered, and concentrated in vacuo. The resulting material was slurried in methanol and filtered to remove a white solid. The filtrate was concentrated in vacuo; LCMS analysis of the resulting material indicated the presence of product: LCMS m/z 219.1 (chlorine isotope pattern observed) $[M+H]^+$. Purification was effected via reversed-phase HPLC (Column: Princeton QB-C18, 5 μm; Mobile phase A: 0.1% formic acid in water; Mobile phase B: 0.1% formic acid in acetonitrile; Gradient: 5% to 100% B), and the product was obtained as a slurry in acetonitrile and water; filtration afforded 10 as a beige crystalline solid (172 mg). $^1$H NMR (400 MHz, methanol-$d_4$) δ 2.48 (br s, 3H).

The filtrate from the reversed-phase purification was extracted with ethyl acetate, and the combined organic layers were dried over sodium sulfate, filtered, and concentrated in vacuo. The resulting solid was triturated with dichloromethane and heptane to afford additional 10 (85.9 mg). $^1$H NMR (400 MHz, methanol-$d_4$) δ 2.48 (d, J=1.0 Hz, 3H).

Combined yield: 258 mg, 1.18 mmol, 28%.

Example 11

5-(4,5-Dichloro-3-methylthiophen-2-yl)-1H-tetrazole (11)

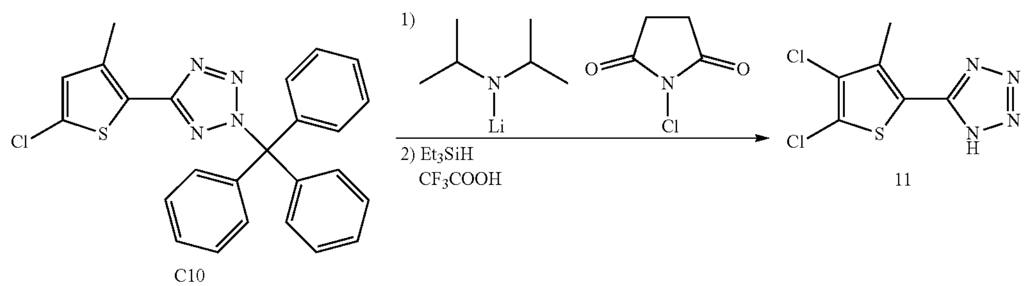

C10

11

To a −78° C. solution of C10 (98.9 mg, 0.223 mmol) in tetrahydrofuran (5 mL) was added a solution of lithium diisopropylamide (2.0 M in tetrahydrofuran/heptane/ethyl benzene, Sigma-Aldrich; 0.223 mL, 0.446 mmol) in a drop-wise manner, at a rate such that the internal reaction temperature did not exceed −70° C. After the reaction mixture had been stirred at −78° C. for 3 hours, a solution of N-chlorosuccinimide (59.6 mg, 0.446 mmol) in tetrahydrofuran (2 mL) was added drop-wise, and stirring was continued at −78° C. for 30 minutes. The reaction mixture was then allowed to reach room temperature over 16 hours, whereupon water (20 mL) was added, and the resulting mixture was extracted with ethyl acetate (2×25 mL). The combined organic layers were washed with saturated aqueous sodium chloride solution (100 mL), dried over sodium sulfate, filtered, and concentrated in vacuo to provide an orange oil, which was dissolved in dichloromethane (5 mL) and treated with trifluoroacetic acid (0.172 mL, 2.23 mmol) followed by triethylsilane (0.178 mL, 1.11 mmol). After this reaction mixture had been stirred at room temperature for 4 hours, it was partitioned between water and dichloromethane. The organic layer was dried over sodium sulfate, filtered, concentrated under reduced pressure, and subjected to reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 30% to 70% B), affording 11 as a solid. Yield: 12 mg, 51 μmol, 23%. LCMS m/z 234.9 (dichloro isotope pattern observed) $[M+H]^+$. $^1$H NMR (400 MHz, chloroform-d) 62.67 (s, 3H).

Example 12

5-(3,5-Dichlorothiophen-2-yl)-1H-tetrazole, ammonium salt (12)

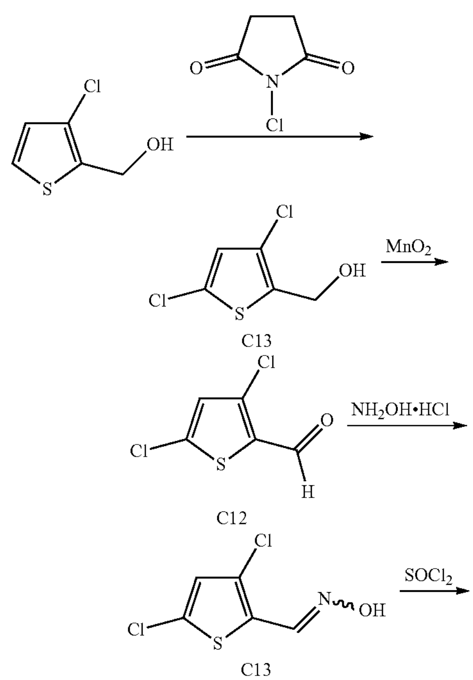

C13

C12

C13

-continued

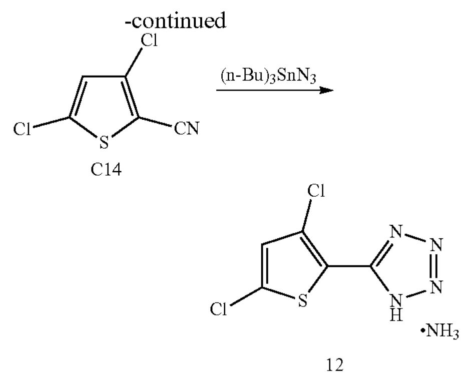

C14

12

Step 1. Synthesis of (3,5-dichlorothiophen-2-yl)methanol (C11)

N-Chlorosuccinimide (1.59 g, 11.9 mmol) was added to a solution of (3-chlorothiophen-2-yl)methanol (1.69 g, 11.4 mmol) in N,N-dimethylformamide (20 mL), and the reaction mixture was stirred at 25° C. for 18 hours. It was then diluted with ethyl acetate (20 mL), washed sequentially with water (3×10 mL) and saturated aqueous sodium chloride solution (10 mL), dried over sodium sulfate, filtered, and concentrated in vacuo to afford C11 as a light yellow oil. Yield: 1.30 g, 7.10 mmol, 62%. $^1$H NMR (400 MHz, chloroform-d) δ 6.75 (s, 1H), 4.74 (s, 2H), 1.97 (br s, 1H).

Step 2. Synthesis of 3,5-dichlorothiophene-2-carbaldehyde (C12)

To a solution of C11 (1.30 g, 7.10 mmol) in dichloromethane (30 mL) was added manganese(IV) oxide (6.17 g, 71.0 mmol). After the reaction mixture had been stirred at 20° C. for 2 hours, it was filtered and concentrated in vacuo, providing C12 as a white solid. Yield: 900 mg, 4.97 mmol, 70%.

Step 3. Synthesis of 3,5-dichlorothiophene-2-carbaldehyde oxime (C13)

To a solution of hydroxylamine hydrochloride (192 mg, 2.76 mmol) in 1-methylpyrrolidin-2-one (5 mL) was added C12 (500 mg, 2.76 mmol). The reaction mixture was heated to 100° C. for 2 hours and then allowed to cool to room temperature, whereupon aqueous sodium bicarbonate solution (50 mL) was added. The resulting mixture was extracted with tert-butyl methyl ether (3×15 mL), and the combined organic layers were washed with saturated aqueous sodium chloride solution, dried over magnesium sulfate, filtered, and concentrated in vacuo to provide C13 (541 mg) as a yellow solid, which was progressed directly to the following step. By $^1$H NMR analysis, this material contained some 1-methylpyrrolidin-2-one, and was judged to be a mixture of E and Z oxime isomers. $^1$H NMR (400 MHz, chloroform-d), product peaks only: δ [8.27 (s) and 7.83 (s), total 1H], [6.89 (s) and 6.80 (s), total 1H].

Step 4. Synthesis of 3,5-dichlorothiophene-2-carbonitrile (C14)

A solution of C13 (from the previous step; 541 mg, 52.76 mmol) in toluene (10 mL) was treated with thionyl chloride (0.401 mL, 5.50 mmol) and the reaction mixture was heated to 100° C. for 20 minutes. Removal of volatiles in vacuo provided C14 (491 mg) as a brown solid, a portion of which was taken directly to the following step. $^{1}H$ NMR (400 MHz, chloroform-d) δ 6.93 (s, 1H).

Step 5. Synthesis of 5-(3,5-dichlorothiophen-2-yl)-1H-tetrazole, ammonium salt (12)

A mixture of C14 (from the previous step: 250 mg, 51.40 mmol) and azidotributylstannane (0.50 mL, 1.8 mmol) was heated at 90° C. for 16 hours, whereupon it was treated with saturated aqueous potassium fluoride solution (20 mL) and stirred for an additional 2 hours. The reaction mixture was then diluted with water (20 mL) and extracted with ethyl acetate (3×15 mL); the combined organic layers were washed with saturated aqueous sodium chloride solution (2×10 mL), dried over sodium sulfate, filtered, and concentrated in vacuo. Silica gel chromatography (Gradient: 0% to 10% methanol in dichloromethane), followed by reversed-phase HPLC (Column: Agela Durashell C18, 5 μm; Mobile phase A: 0.05% ammonium hydroxide in water; Mobile phase B: acetonitrile; Gradient: 0% to 60% B), afforded 12 as a white solid. Yield: 13.4 mg, 56.3 μmol, 4% over 3 steps. LCMS m/z 220.6 (dichloro isotope pattern observed) $[M+H]^+$. $^{1}H$ NMR (400 MHz, DMSO-$d_6$) δ 7.27 (s, 1H), 7.24 (br s, 1H), 7.11 (br s, 1H), 6.99 (br s, 1H).

Example 13

5-(3-Bromo-5-ethylthiophen-2-yl)-1H-tetrazole (13)

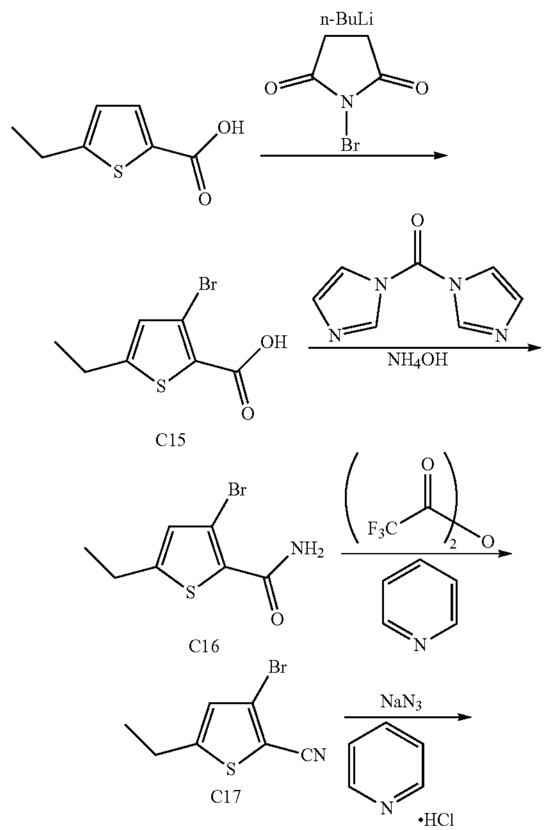

-continued

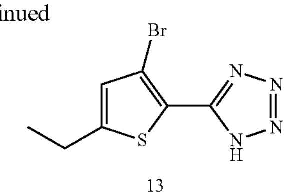

13

Step 1. Synthesis of 3-bromo-5-ethylthiophene-2-carboxylic acid (C15)

To a −65° C. solution of 5-ethylthiophene-2-carboxylic acid (835 mg, 5.35 mmol) in tetrahydrofuran (10 mL) was added a solution containing n-butyllithium (856 mg, 13.4 mmol). The reaction mixture was stirred at −65° C. for 3 hours, whereupon a solution of N-bromosuccinimide (1.43 g, 8.03 mmol) in tetrahydrofuran (10 mL) was added at −65° C. After the addition, the reaction mixture was slowly warmed to 15° C. and stirred at 15° C. for 16 hours, at which time it was adjusted to pH 4 by addition of 1 M hydrochloric acid. Water (10 mL) was added, and the resulting mixture was extracted with ethyl acetate (3×30 mL); the combined organic layers were dried over sodium sulfate, filtered, and concentrated in vacuo to provide C15 as a brown gum (1.26 g), which was used directly in the following step. LCMS m/z 237.0 (bromine isotope pattern observed) $[M+H]^+$.

Step 2. Synthesis of 3-bromo-5-ethylthiophene-2-carboxamide (C16)

A mixture of C15 (from the previous step; 1.26 g, 55.35 mmol) and 1,1'-carbonyldiimidazole (1.30 g, 8.02 mmol) in N,N-dimethylformamide (15 mL) was stirred at 25° C. for 2 hours. The reaction mixture was then poured into ammonium hydroxide solution (20 mL), stirred for 20 minutes, and extracted with ethyl acetate (3×10 mL). The combined organic layers were washed with saturated aqueous sodium chloride solution (4×10 mL), dried over sodium sulfate, filtered, and concentrated in vacuo; chromatography on silica gel (Gradient: 0% to 75% ethyl acetate in petroleum ether) afforded C16 as a white solid. Yield: 475 mg, 2.03 mmol, 38% over 2 steps. $^{1}H$ NMR (400 MHz, DMSO-$d_6$) δ 7.80-7.60 (br s, 1H), 7.47-7.29 (br s, 1H), 6.95 (s, 1H), 2.79 (q, J=7.5 Hz, 2H), 1.22 (t, J=7.5 Hz, 3H).

Step 3. Synthesis of 3-bromo-5-ethylthiophene-2-carbonitrile (C17)

To a 0° C. solution of C16 (475 mg, 2.03 mmol) and pyridine (0.225 mg, 2.84 mmol) in dichloromethane (10 mL) was added trifluoroacetic anhydride (511 mg, 2.43 mmol). The reaction mixture was stirred at 20° C. for 1 hour, whereupon it was diluted with dichloromethane (10 mL) and washed sequentially with water (3×5 mL) and saturated aqueous sodium chloride solution (3×5 mL). After the organic layer had been dried over sodium sulfate, it was filtered, then concentrated in vacuo to provide C17 as a brown oil. Yield: 440 mg, 2.04 mmol, quantitative. $^{1}H$ NMR (400 MHz, chloroform-d) δ 6.81 (t, J=1.1 Hz, 1H), 2.87 (qd, J=7.5, 1.1 Hz, 2H), 1.33 (t, J=7.5 Hz, 3H).

Step 4. Synthesis of 5-(3-bromo-5-ethylthiophen-2-yl)-1H-tetrazole (13)

A mixture of C17 (100 mg, 0.463 mmol), sodium azide (36.1 mg, 0.555 mmol), and pyridine hydrochloride (53.5 mg, 0.463 mmol) in N,N-dimethylformamide (2 mL) was stirred at 110° C. for 16 hours. The reaction mixture was then diluted with saturated aqueous sodium chloride solution (20 mL) and extracted with ethyl acetate (3×5 mL); the combined organic layers were concentrated in vacuo and purified via reversed-phase HPLC (Column: YMC-Actus Triart C18, 7 μm; Mobile phase A: water containing 0.225% formic acid; Mobile phase B: acetonitrile; Gradient: 38% to 58% B), affording 13 as a yellow solid. Yield: 16.7 mg, 64.4 μmol, 14%. LCMS m/z 259.2 (bromine isotope pattern observed) $[M+H]^+$. $^1H$ NMR (400 MHz, DMSO-$d_6$) δ 7.12 (s, 1H), 2.88 (q, J=7.5 Hz, 2H), 1.27 (t, J=7.5 Hz, 3H).

The examples in Table 1 were made by processes analogous to those used in synthesizing the Example(s) identified. Appropriate analogous starting materials were employed, including the specific compounds cited below. In the column titled "Method of synthesis; Non-commercial starting materials" typically the Method of Synthesis is described by providing an Example and where appropriate, after the "semicolon", a non-commercial starting material is described by reference to e.g., an Example.

TABLE 1

Method of preparation, structure, and physicochemical data for Examples 14-37.

| Example Number | Method of synthesis; Non-commercial starting materials | Structure | $^1H$ NMR; Mass spectrum, observed ion m/z $[M + H]^+$ or HPLC retention time; Mass spectrum m/z $[M + H]^+$ (unless otherwise indicated) |
|---|---|---|---|
| 14 | Example 12[1] | 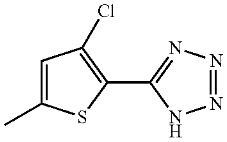 | $^1H$ NMR (400 MHz, DMSO-$d_6$) δ 7.06 (m, 1H), 2.53-2.51 (brs, 3H); 201.1 (chlorine isotope pattern observed) |
| 15 | Example 13[2,3] | 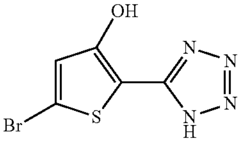 [SMILES: Oc1cc(Br)sc1-c1nnn[nH]1] | $^1H$ NMR (400 MHz, methanol-$d_4$) δ 7.66 (s, 1H); 247.1 (bromine isotope pattern observed) |
| 16 | Example 13[2,3] | 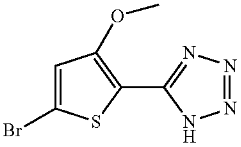 | $^1H$ NMR (400 MHz, methanol-$d_4$) δ 7.70 (s, 1H), 3.97 (s, 3H); 261.0 (bromine isotope pattern observed) |
| 17 | Example 1; C5 | 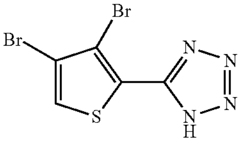 [SMILES: Brc1csc(-c2nnn[nH]2)c1Br] | $^1H$ NMR (400 MHz, DMSO-$d_6$) δ 8.19 (s, 1H); 310.8 (dibromo isotope pattern observed) |
| 18 | Example 1; C1 | 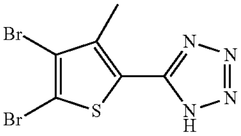 | $^1H$ NMR (400 MHz, DMSO-$d_6$) δ 2.54 (s, 3H); 324.7 (dibromo isotope pattern observed) |
| 19 | Example 6 | 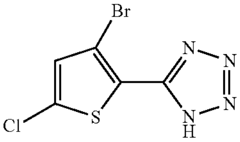 [SMILES: Clc1cc(Br)c(-c2nnn[nH]2)s1] | $^1H$ NMR (400 MHz, methanol-$d_4$) δ 7.18 (s, 1H); 266.8 (bromo chloro isotope pattern observed) |
| 20 | Example 1[4] | 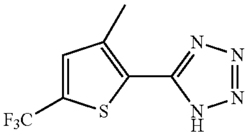 | $^1H$ NMR (400 MHz, DMSO-$d_6$) δ 7.62 (s, 1H), 2.56 (s, 3H); 235.1 |

TABLE 1-continued

| Example Number | Method of synthesis; Non-commercial starting materials | Structure | $^1$H NMR; Mass spectrum, observed ion m/z $[M + H]^+$ or HPLC retention time; Mass spectrum m/z $[M + H]^+$ (unless otherwise indicated) |
|---|---|---|---|
| Method of preparation, structure, and physicochemical data for Examples 14-37. | | | |
| 21 | Example 1[5] | 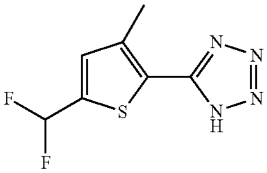 | $^1$H NMR (400 MHz, methanol-$d_4$) δ 7.33 (br s, 1H), 7.03 (t, $J_{HF}$ = 55.5 Hz, 1H), 2.57 (s, 3H); 217.1 |
| 22 | Example 1[6] | 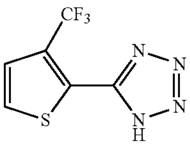 [SMILES: FC(F)(F)c1ccsc1-c1nnn[nH]1] | $^1$H NMR (400 MHz, DMSO-$d_6$) δ 8.05 (d, J = 5.3 Hz, 1H), 7.57 (d, J = 5.3 Hz, 1H); LCMS m/z 219.1 $[M - H^+]$ |
| 23 | Example 6; Example 22 | 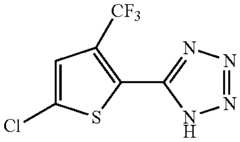 | $^1$H NMR (400 MHz, DMSO-$d_6$) δ 7.52 (s, 1H); LCMS m/z 253.1 (chlorine isotope pattern observed) $[M - H^+]$ |
| 24 | Example 12[7] | 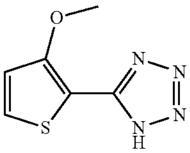 | $^1$H NMR (400 MHz, chloroform-d) δ 12.53 (br s, 1H), 7.53 (d, J= 5.5 Hz, 1H), 6.97 (d, J = 5.5 Hz, 1H), 4.13 (s, 3H); 183.1 |
| 25 | Examples 3 and 4 | 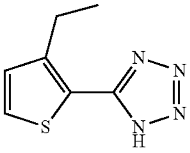 | $^1$H NMR (400 MHz, DMSO-$d_6$) δ 7.76 (d, J = 5.1 Hz, 1H), 7.18 (d, J = 5.1 Hz, 1H), 2.97 (q, J = 7.5 Hz, 2H), 1.19 (t, J = 7.5 Hz, 3H); 181.1 |
| 26 | Examples 3 and 4 | 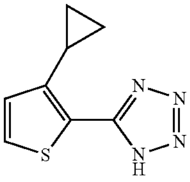 [SMILES: c1cc(C2CC2)c(-c2nnn[nH]2)s1] | $^1$H NMR (400 MHz, DMSO-$d_6$) δ 7.71 (d, J = 5.3 Hz, 1H), 6.81 (d, J = 5.3 Hz, 1H), 2.76-2.67 (m, 1H), 1.10-1.00 (m, 2H), 0.80-0.72 (m, 2H); 193.1 |
| 27 | Example 6; Example 25 | 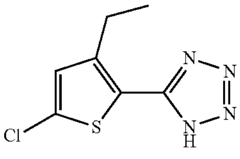 | $^1$H NMR (400 MHz, DMSO-$d_6$) δ 7.26 (s, 1H), 2.93 (q, J = 7.5 Hz, 2H), 1.18 (t, J = 7.5 Hz, 3H); LCMS m/z 213.1 (chlorine isotope pattern observed) $[M - H^+]$ |
| 28 | Example 1 | 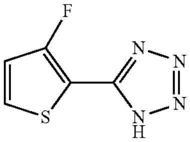 [SMILES: Fc1ccsc1-c1nnn[nH]1] | $^1$H NMR (400 MHz, chloroform-d) δ 7.52 (dd, J = 5.6, 4.1 Hz, 1H), 7.00 (d, J = 5.6 Hz, 1H); 171.0 |

TABLE 1-continued

Method of preparation, structure, and physicochemical data for Examples 14-37.

| Example Number | Method of synthesis; Non-commercial starting materials | Structure | $^1$H NMR; Mass spectrum, observed ion m/z [M + H]$^+$ or HPLC retention time; Mass spectrum m/z [M + H]$^+$ (unless otherwise indicated) |
|---|---|---|---|
| 29 | Example 6; Example 26 | 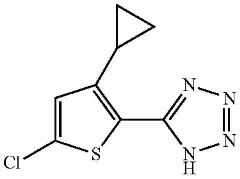 [SMILES: Clc1cc(C2CC2)c(-c2nnn[nH]2)s1] | $^1$H NMR (400 MHz, DMSO-$d_6$) δ 6.86 (s, 1H), 2.84-2.73 (m, 1H), 1.07-0.98 (m, 2H), 0.81-0.74 (m, 2H); LCMS m/z 225.1 (chlorine isotope pattern observed) [M − H$^+$] |
| 30 | Example 6; Example 28 | 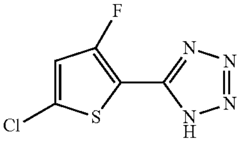 [SMILES: Fc1cc(Cl)sc1-c1nnn[nH]1] | 1.96 minutes[8]; 205.1 (chlorine isotope pattern observed) |
| 31 | Example 2; 7 | 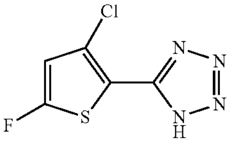 | $^1$H NMR (400 MHz, DMSO-$d_6$) δ 7.20 (d, J = 2.0 Hz, 1H); 205.1 (chlorine isotope pattern observed) |
| 32 | Example 1[9]; C17 | 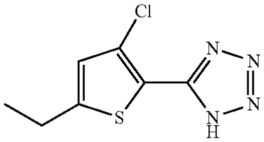 | $^1$H NMR (400 MHz, DMSO-$d_6$) δ 6.87 (s, 1H), 2.83 (qd, J = 7.6, 1.0 Hz, 2H), 2.45 (s, 3H), 1.26 (t, J = 7.5 Hz, 3H); 195.3 |
| 33 | Example 12[10] | 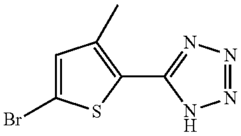 | $^1$H NMR (400 MHz, methanol-$d_4$) δ 7.11 (s, 1H), 2.53 (s, 3H); 244.9 (bromine isotope pattern observed) |
| 34 | Example 2 | 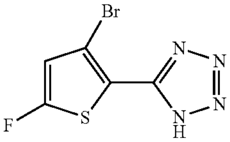 [SMILES: Fc1cc(Br)c(-c2nnn[nH]2)s1] | 2.12 minutes[8]; 248.9 (bromine isotope pattern observed) |
| 35 | Example 1 | 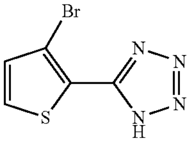 [SMILES: Brc1ccsc1-c1nnn[nH]1] | $^1$H NMR (400 MHz, chloroform-d) δ 7.59 (d, J = 5.3 Hz, 1H), 7.18 (d, J = 5.3 Hz, 1H); 232.9 (bromine isotope pattern observed) |
| 36 | Example 1 | 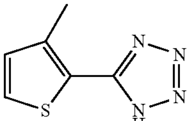 | $^1$H NMR (400 MHz, DMSO-$d_6$) δ 7.74 (d, J = 5.0 Hz, 1H), 7.11 (d, J= 5.0 Hz, 1H), 2.51 (s, 3H); 167.3 |

TABLE 1-continued

| Example Number | Method of synthesis; Non-commercial starting materials | Structure | $^1$H NMR; Mass spectrum, observed ion m/z [M + H]$^+$ or HPLC retention time; Mass spectrum m/z [M + H]$^+$ (unless otherwise indicated) |
|---|---|---|---|
| Method of preparation, structure, and physicochemical data for Examples 14-37. | | | |
| 37 | Example 24[11] | 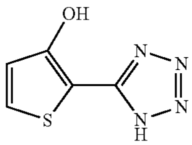 [SMILES: Oc1ccsc1-c1nnn[nH]1] | $^1$H NMR (400 MHz, methanol-$d_4$) δ 7.56 (d, J = 5.4 Hz, 1H), 6.81 (d, J = 5.4 Hz, 1H); 169.2 |

1. 3-Chloro-5-methylthiophene-2-carboxylic acid was converted to the requisite 3-chloro-5-methylthiophene-2-carbonitrile using the method described in Example 13 forsynthesis of C17 from C15.
2. Sodium hydroxide-mediated hydrolysis of methyl 5-bromo-3-methoxythiophene-2-carboxylate provided starting material 5-bromo-3-methoxythiophene-2-carboylic acid
3. During the tetrazole formation, partial cleavage of the methyl ether occurred, providing both Examples 15 and 16 as products.
4. (5-Cyano-4-methylthiophen-2-yl)boronic acid was converted to the requisite 3-methyl-5-(trifluoromethyl)thiophene-2-carbonitrile using the method of Y. Ye et al., *Organic Lett.* 2012, 14, 4979-4981.
5. Reaction of 3-methylthiophene-2-carbonitrile with lithium diisopropylamide, followed by N,N-dimethylformamide, provided 5-formyl-3-methylthiophene-2-carbonitrile; this material was treated with (diethylamino)sulfur trifluoride to afford the requisite 5-(difluoromethyl)-3-methylthiophene-2-carbonitrile.
6. 3-Bromothiophene-2-carbonitrile was reacted with methyl difluoro(fluorosulfonyl)acetate and copper(I) iodide at elevated temperature to afford the requisite 3-(trifluoromethyl)thiophene-2-carbonitrile.
7. Sodium hydroxide-mediated hydrolysis of methyl 3-methoxythiophene-2-carboxylate provided 3-methoxythiophene-2-carboxylic acid, which was converted to 3-methoxythiophene-2-carbonitrile using the method described in Example 13 for synthesis of C17 from C15.
8. Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.
9. Conversion of C17 to the requisite 5-ethyl-3-methylthiophene-2-carbonitrile was carried out by reaction with trimethylboroxine and cesium carbonate in the presence of [1,1'-bis(di-tert-butylphosphino)ferrocene]dichloropalladium (II) at elevated temperature.
10. 5-Bromo-3-methylthiophene-2-carbonitrile was synthesized from 5-bromo-3-methylthiophene-2-carboxylic acid using the method described in Example 13 for conversion of C15 to C17.
11. Cleavage of the methyl ether of Example 24 with boron tribromide afforded Example 37.

The following protocols may of course be varied by those skilled in the art.

Protein Generation

BCKDK protein was generated using a pET vector containing from N- to C-terminus: 6×His, MBP, a TEV protease site (ENLYFQG), a biotin acceptor peptide (GLNDIFEAQKIEWHE), and human BCKDK (residues 31-412 of the protein pre-processing). Protein was co-expressed with GroEL-GroES in BL21(DE3) *E. coli* in LB media, and protein production was induced with 0.5 mM IPTG and 0.5 mg/mL L-arabinose at an OD600 of 1 and grown for 16 h at 26° C. Bacteria were lysed using a Microfluidizer in 100 mM potassium phosphate pH 7.5, 500 mM NaCl, 0.1 mM EDTA, 1% Tween-20, 0.25% Triton X-100, 10% glycerol, 1 mM DTT, and protease inhibitors. MBP-tagged protein was purified by affinity chromatography using amylose resin, and MBP was removed from BCKDK by TEV protease incubation followed by gel filtration chromatography in 50 mM HEPES pH 7.5, 500 mM NaCl, 300 mM L-Arginine, 2 mM $MgCl_2$, 1 mM DTT, and 10% glycerol.

A pET vector containing *E. coli* LplA was expressed in BL21(DE3) *E. coli* in LB media, and protein production was induced with 0.75 mM IPTG at an $OD_{600}$ of 1 and grown for 16 h at 30° C. Bacteria were lysed using a Microfluidizer in 50 mM sodium phosphate buffer pH 7.5, 350 mM NaCl, 1.5 mM $MgCl_2$, and 1 mM DTT. LplA protein was precipitated from clarified lysate with 1 M ammonium sulfate and further purified by gel filtration chromatography in 50 mM sodium phosphate pH 7.5, 350 mM NaCl, 1.5 mM $MgCl_2$, 1 mM DTT, and 10% glycerol.

The BCKDHE1α-E2 fusion substrate was cloned into a pET vector and contained from N- to C-terminus: the lipoyl binding domain of E2 (residues 62-160 pre-processing), a TEV protease site (LENLYFQG), residues 331-345 (pre-processing) from E1α, and 6×His (Tso, S. C. et al., J Biol Chem 2014, 289 (30), 20583-20593). The fusion substrate was expressed in BL21(DE3) *E. coli* in LB media, and protein production was induced with 0.75 mM IPTG at an $OD_{600}$ of 1 and grown for 16 h at 30° C. Bacteria were lysed using a Microfluidizer in 50 mM sodium phosphate pH 7.5, 350 mM NaCl, 10 mM imidazole, 10% glycerol, 1 mM DTT, and protease inhibitors. Fusion substrate was purified by Ni-NTA affinity chromatography followed gel filtration chromatography in 50 mM sodium phosphate pH 7.5, 350 mM NaCl, 1.5 mM $MgCl_2$, 1 mM DTT, and 10% glycerol. For lipoylation, fusion substrate was incubated with LplA at a 10:1 (substrate:LplA) ratio in 20 mM sodium phosphate pH 7.4, 6 mM $MgCl_2$, 4 mM ATP, 2 mM DTT, 3 mM DL-6,8-thioctic acid at 37° C. The reaction was monitored using an Agilent 6530 Q-TOF coupled to an Agilent 1290 UPLC. The final lipoylated fusion substrate was purified by gel filtration chromatography in 50 mM HEPES pH 7.5, 350 mM NaCl, 1.5 mM $MgCl_2$, 1 mM DTT, 10% glycerol.

In Vitro FRET

BCKDK activity was monitored by phosphorylation of a HIS-tagged fusion BCKDHE1α-E2 substrate protein as described above and was detected using a time resolved-fluorescence resonance energy transfer (TR-FRET) assay system. Compounds were spotted into a 384 well plate, and purified human BCKDK protein was added to the plated compound. After incubation, the LBD-linker-E1 phosphorylation sequence was added in the presence of 15 μM ATP. The reaction was terminated with EDTA. Phosphorylated substrate was recognized by the addition of rabbit anti-E1 phospho Ser293 antibodies (Bethyl Laboratories—A304-672A), and the TR-FRET signal was developed by addition of anti-HIS donor molecules (Europium; Perkin Elmer—AD0205, AD0110, AD0111) and anti-Rabbit acceptor molecules (Ulight; Perkin Elmer—TRF502D, TRF502M, TRF502R). Recognition of phosphorylated E1 brought donor and acceptor molecules into close proximity, and excitation at 320 nm caused energy transfer from the Europium donor to the Ulight acceptor dye, which in turn generated light at 665 nm. Signal intensity was proportional to the level of BCKDK-mediated substrate phosphorylation. Reactions were normalized to zero percent effect with DMSO and one hundred percent effect with 600 µM Radicicol, a known BCKDK inhibitor. IC50 curves were generated using ABASE software (IDBS, Boston MA).

In Table 2 assay data ($IC_{50}$s) are presented for the Examples below in accordance with the above-described assay (to two (2) significant figures as the geometric mean, based on the number of replicates tested (Number)).

TABLE 2

Biological activity and IUPAC name for Examples 1-37.

| Example Number | In Vitro FRET $IC_{50}$ (µM) | Number | IUPAC Name |
|---|---|---|---|
| 1 | 1.9 | 7 | 5-(4-bromo-3-methylthiophen-2-yl)-1H-tetrazole |
| 2 | 3.6 | 4 | 5-(5-fluoro-3-methylthiophen-2-yl)-1H-tetrazole |
| 3 | 1.1 | 6 | 5-(4-chloro-3-ethylthiophen-2-yl)-1H-tetrazole, ammonium salt |
| 4 | 1.1 | 4 | 5-(4-bromo-3-ethylthiophen-2-yl)-1H-tetrazole, ammonium salt |
| 5 | 2.5 | 3 | 5-[3-(difluoromethyl)thiophen-2-yl]-1H-tetrazole |
| 6 | 1.1 | 7 | 5-[5-chloro-3-(difluoromethyl)thiophen-2-yl]-1H-tetrazole |
| 7 | 11 | 3 | 5-(3-chlorothiophen-2-yl)-1H-tetrazole |
| 8 | 3.4 | 3 | 5-(5-bromo-3-chlorothiophen-2-yl)-1H-tetrazole |
| 9 | 1.4 | 6 | 5-(5-chloro-3-methylthiophen-2-yl)-1H-tetrazole |
| 10 | 0.81 | 9 | 5-(5-chloro-4-fluoro-3-methylthiophen-2-yl)-1H-tetrazole |
| 11 | 1.9 | 3 | 5-(4,5-dichloro-3-methylthiophen-2-yl)-1H-tetrazole |
| 12 | 2.0 | 4 | 5-(3,5-dichlorothiophen-2-yl)-1H-tetrazole, ammonium salt |
| 13 | >83 | 4 | 5-(3-bromo-5-ethylthiophen-2-yl)-1H-tetrazole |
| 14 | 2.6 | 4 | 5-(3-chloro-5-methylthiophen-2-yl)-1H-tetrazole |
| 15 | 13 | 4 | 5-bromo-2-(1H-tetrazol-5-yl)thiophene-3-ol |
| 16 | 4.5 | 3 | 5-(5-bromo-3-methoxythiophen-2-yl)-1H-tetrazole |
| 17 | 6.1 | 5 | 5-(3,4-dibromothiophen-2-yl)-1H-tetrazole |
| 18 | 4.5 | 3 | 5-(4,5-dibromo-3-methylthiophen-2-yl)-1H-tetrazole |
| 19 | 4.1 | 3 | 5-(3-bromo-5-chlorothiophen-2-yl)-1H-tetrazole |
| 20 | 3.7 | 3 | 5-[3-methyl-5-(trifluoromethyl)thiophen-2-yl]-1H-tetrazole |
| 21 | 3.6 | 3 | 5-[5-(difluoromethyl)-3-methylthiophen-2-yl]-1H-tetrazole |
| 22 | 11 | 3 | 5-[3-(trifluoromethyl)thiophen-2-yl]-1H-tetrazole |
| 23 | 7.2 | 3 | 5-[5-chloro-3-(trifluoromethyl)thiophen-2-yl]-1H-tetrazole |
| 24 | >300 | 3 | 5-(3-methoxythiophen-2-yl)-1H-tetrazole |
| 25 | 9.8 | 3 | 5-(3-ethylthiophen-2-yl)-1H-tetrazole |
| 26 | >300 | 3 | 5-(3-cyclopropylthiophen-2-yl)-1H-tetrazole |
| 27 | 4.0 | 3 | 5-(5-chloro-3-ethylthiophen-2-yl)-1H-tetrazole |
| 28 | 16 | 3 | 5-(3-fluorothiophen-2-yl)-1H-tetrazole |
| 29 | 10 | 3 | 5-(5-chloro-3-cyclopropylthiophen-2-yl)-1H-tetrazole |
| 30 | 2.9 | 3 | 5-(5-chloro-3-fluorothiophen-2-yl)-1H-tetrazole |
| 31 | 3.6 | 3 | 5-(3-chloro-5-fluorothiophen-2-yl)-1H-tetrazole |
| 32 | 15 | 4 | 5-(5-ethyl-3-methylthiophen-2-yl)-1H-tetrazole |
| 33 | 3.1 | 3 | 5-(5-bromo-3-methylthiophen-2-yl)-1H-tetrazole |
| 34 | 2.7 | 3 | 5-(3-bromo-5-fluorothiophen-2-yl)-1H-tetrazole |
| 35 | 1.4 | 3 | 5-(3-bromothiophen-2-yl)-1H-tetrazole |
| 36 | 6.0 | 4 | 5-(3-methylthiophen-2-yl)-1H-tetrazole |
| 37 | 13 | 3 | 2-(1H-tetrazol-5-yl)thiophene-3-ol |

Phospho BCKDHA AlphaLISA

Prior to conducting the assay, BCKDH antibodies (Bethyl A303-790A) were biotinylated using the ChromaLink™ One-Shot Antibody Biotinylation Kit B-9007-009K and phospho Ser293 BCKDHA antibodies (Bethyl A304-672A) were directly conjugated to AlphaLISA Acceptor Beads (custom conjugation performed by Perkin Elmer's Lance/Delfia Custom Services, Boston MA). Human skeletal myocytes (Gibco A11440) were plated in a 384 well plate at a density of 7500 live cells/well and grown in skeletal muscle growth media containing the media supplement and chick embryo extract (Promocell C-23060 and C-23160, MP92850145). After overnight incubation, media was removed, and BCKDK inhibitors were added in assay media (growth media diluted 10-fold in PBS). After 60 minutes, the media was removed, the cells were washed with PBS and lysed in 10 μL of buffer (Cell Signaling #9803) containing 2 nM biotinylated total BCKDH antibodies. Samples were incubated for 60 minutes, and 5 μL of AlphaLISA acceptor beads conjugated with phospho-S293 BCKDH antibodies were added 1× Alpha buffer. After a 60 minute incubation, 5 μL streptavidin donor beads (40 μg/μL) beads were added in 1× Alpha buffer while protecting from light. Fluorescence was emitted when the phospho and total BCKDH antibodies were within proximity, signifying phosphorylation of S293 BCKDH. Fluorescence was monitored on the Envision plate reader. The zero percent effect was determined from DMSO treatment and the maximal effect was assessed relative to the BCKDK inhibitor BT2. (Tso, S. C.; Gui, W. J.; Wu, C. Y.; et al. Benzothiophene carboxylate derivatives as novel allosteric inhibitors of branched-chain alpha-ketoacid dehydrogenase kinase. J Biol Chem 2014, 289, 20583-20593). $IC_{50}$ curves were generated using ActivityBase software (IDBS, Boston MA). The $IC_{50}$ for the following compounds were determined: Example 1 18±2.3 μM (n=5), Example 9 11±0.87 μM (n=2).

Diabetic Animal Model

Mice fed 60% high fat diet (Research Diets 12492) were dosed PO with Example 1 for one day, fasted overnight, and blood glucose was measured with an alpha track glucometer. The animals were dosed again PO with Example 1 the next morning, and one hour later, blood glucose was measured again immediately using an alpha track glucometer (Zoetis, Parsippany, NJ) to assess fasting glucose levels prior to oral gavage of 1 g/kg dextrose. Blood glucose was measured 15, 30, 60, and 120 minutes after the gavage, and the data were plotted and analyzed as area under the curve using GraphPad Prism 8.0 (GraphPad Software, La Jolla, CA). For animals that were dosed with vehicle or Example 1 as above, mean±SEM fasting plasma glucose levels were 185±18 (vehicle, n=7), 194±14 (3 mg/kg, n=9), 160±11 (10 mg/kg, n=10), 136±9 mg/dL (30 mg/kg, n=9). Area under the curve for the glucose tolerance test as percent of vehicle treated group was 100.0±7 (vehicle, n=7), 106±9 (3 mg/kg, n=9), 99±2 (10 mg/kg, n=10), 72±4 (30 mg/kg, n=9).

Heart Failure Rat Model

Dahl salt sensitive male rats (Charles River strain SS/JrHsdMcwiCrl) were fed control diet or 6% high salt diet (iD03121701-AIN-76a rodent diet with added 6% NaCl) for 21 weeks in total. At week 5, the high salt diet-fed rats were dosed PO with 100 mg/kg BT2 or vehicle once daily for the last 16 weeks of study. Echocardiography was performed at week 18 (myocardial performance index (MPI): control diet 0.567±0.034, high salt+vehicle 0.810±0.039, high salt+BT2 0.660±0.030; Isovolumic relaxation time (IVRT): control diet 23.154±0.60 ms, high salt+vehicle 36.507±2.20 ms, high salt+BT2 31.605±1.78 ms; Intraventricular septal thickness at diastole (IVDd): control 2.03±0.088 mm, high salt+vehicle 2.877±0.110 mm, high salt+BT2 2.489±0.089 mm). NT-pro-BNP (MSD K153JKD; control 294.9±26.04 μg/mL, high salt+vehicle 1003.0±200.8 μg/mL, high salt+BT2 503.4±84.96 μg/mL), and proANP (MSD K153MBD; control 33.50±5.4 ng/mL, high salt 65.19±8.3 ng/mL, high salt+BT2 38.81±7.0 ng/mL) levels were measured in plasma using MSD assays at the terminal time point. Heart weights were measured at euthanasia and normalized to tibia length (heart/tibia control 0.033±0.001 g/mm; high salt+vehicle 0.042±0.001 g/mm, high salt+BT2 0.038±0.001 g/mm).

Heart Failure Mouse Model

Male adult mice (8-16-week-old, Charles River strain C57BL6/NCrl) were used for transverse aortic constriction. One week prior to surgery, animals were dosed with BT2 (40 mg/kg) or vehicle. On the day of surgery, animals were anesthetized, the chest cavity was opened, the aortic area was cleaned, and a silk suture was placed around the transverse aorta. Sham mice were not tied, and TAC mice had the suture tied around a needle. Mice were allowed to recover and were dosed either orally with BT2 (40 mg/kg) once daily or vehicle. Echocardiography was performed serially. Heart weights and lung weights were measured at euthanasia. Data obtained with BT2 have been reported in Sun et al, Circulation. 2016 May 24; 133(21):2038-49. doi: 10.1161/CIRCULATIONAHA.115.020226.

Powder X-ray Diffraction

Figure 2:
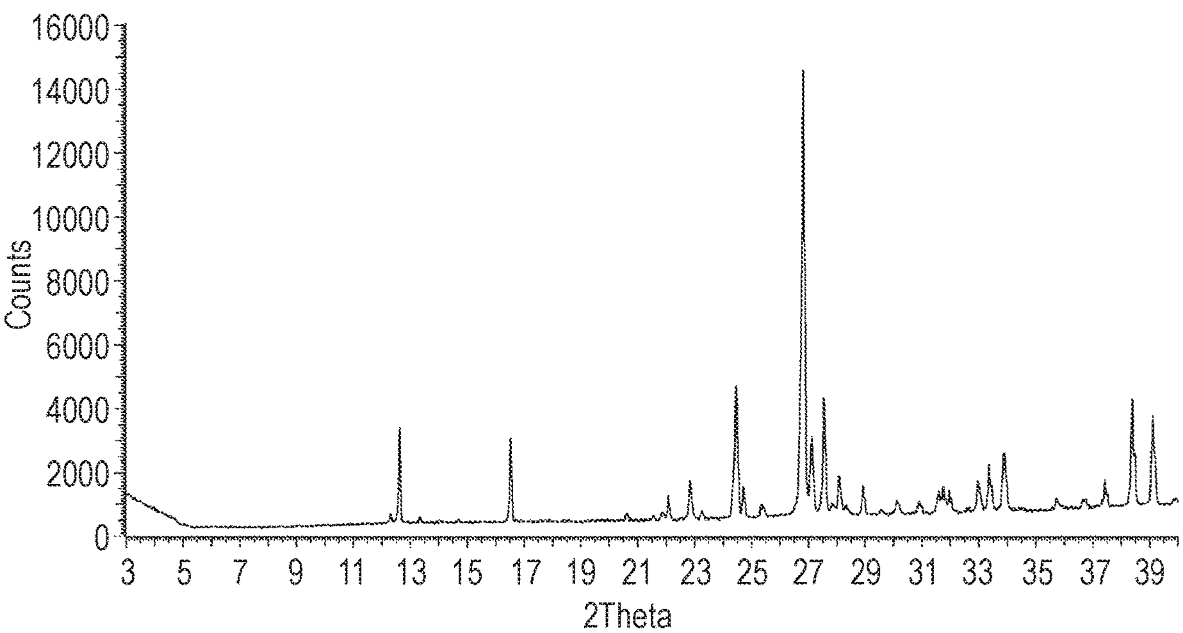
FIG. 2 is a characteristic x-ray powder diffraction pattern showing a crystalline form of Example 10, Form 1 (Vertical Axis: Intensity (CPS); Horizontal Axis: Two theta (degrees)).

Powder X-ray diffraction analysis for the compound of Example 6 (the reaction conditions and isolation conditions were analogous to Example 6) and Example 10 were conducted using a Bruker AXS D8 Endeavor diffractometer equipped with a Cu radiation source. The divergence slit was set at 3 mm continuous illumination. Diffracted radiation was detected by a PSD-Lynx Eye detector, with the detector PSD opening set at 4.105 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.020 degrees and a step time of 0.5 second. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position from PXRD stated in USP up to +/−0.2° 2-Theta (USP-941). Characteristic x-ray powder diffraction patterns are provided in FIGS. 1 and 2. The PXRD data from these figures are further described below.

TABLE 3a

| Key PXRD peaks to characterize crystalline material of Example 6, Form 1 and Example 10, Form 1 | |
|---|---|
| Example 6, Form 1 | Example 10, Form 1 |
| Angle 2Θ (°)<br>10.6, 15.9, 23.5, 32.1 | Angle 2Θ (°)<br>24.5, 26.8, 33.9, 39.1 |

TABLE 3b

| PXRD peaks for crystalline material of Example 6, Form 1 | | | | | |
|---|---|---|---|---|---|
| Angle 2Θ (°) | Relative intensity (%) | Angle 2Θ (°) | Relative intensity (%) | Angle 2Θ (°) | Relative intensity (%) |
| 10.6 | 33 | 26.7 | 44 | 33.5 | 14 |
| 11.6 | 4 | 27.4 | 17 | 35.0 | 28 |
| 15.2 | 22 | 28.1 | 17 | 35.3 | 30 |
| 15.9 | 100 | 28.4 | 27 | 36.1 | 24 |
| 21.3 | 26 | 28.7 | 19 | 36.9 | 7 |
| 23.5 | 79 | 29.2 | 23 | 37.3 | 11 |
| 24.2 | 7 | 29.9 | 49 | 37.7 | 65 |
| 25.1 | 23 | 31.1 | 4 | 37.8 | 33 |
| 25.6 | 24 | 31.7 | 25 | 38.7 | 9 |
| 25.9 | 20 | 32.1 | 91 | 39.9 | 7 |
| 26.3 | 26 | 32.9 | 21 | | |

TABLE 3c

| PXRD peaks for crystalline material of Example 10, Form 1 | | | |
|---|---|---|---|
| Angle 2Θ (°) | Relative intensity (%) | Angle 2Θ (°) | Relative intensity (%) |
| 12.6 | 21.0 | 28.9 | 6.6 |
| 16.5 | 18.7 | 30.1 | 3.1 |
| 22.1 | 5.5 | 31.6 | 5.1 |
| 22.8 | 8.1 | 31.8 | 5.9 |
| 24.5 | 29.4 | 32.0 | 5.0 |
| 24.7 | 7.1 | 33.0 | 6.9 |
| 25.4 | 26.2 | 33.4 | 10.6 |
| 26.8 | 100.0 | 33.9 | 13.2 |
| 27.1 | 17.8 | 37.4 | 6.0 |
| 27.5 | 26.2 | 38.4 | 24.0 |
| 28.1 | 8.8 | 39.1 | 20.4 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A compound of Formula I

Formula I

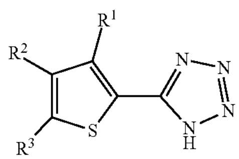

wherein $R^1$ is fluoro, chloro, amino, cyano, ethynyl, $(C_1-C_4)$alkyl, $(C_3-C_4)$cycloalkyl, $(C_1-C_4)$alkoxy, $(C_1-C_4)$fluoroalkyl or $(C_1-C_4)$fluoroalkoxy; wherein when $R^2$ is H and $R^3$ is H, $R^1$ is fluoro, chloro, amino, cyano, ethynyl, $(C_2-C_4)$alkyl, $(C_3-C_4)$cycloalkyl, $(C_1-C_4)$alkoxy, $(C_1-C_4)$fluoroalkyl or $(C_1-C_4)$fluoroalkoxy;

$R^2$ is H, fluoro, chloro, bromo, hydroxyl, amino, cyano, ethynyl, $(C_1-C_4)$alkyl, $(C_3-C_4)$cycloalkyl, $(C_1-C_4)$alkoxy, $C_1-C_4)$fluoroalkyl, or $(C_1-C_4)$fluoroalkoxy; and $R^3$ is H, fluoro, chloro, bromo, hydroxyl, amino, cyano, ethynyl, $(C_1-C_4)$alkyl, $(C_3-C_4)$cycloalkyl, $(C_1-C_4)$alkoxy, $(C_1-C_4)$fluoroalkyl or $(C_1-C_4)$fluoroalkoxy;

or a pharmaceutically acceptable salt of said compound.

2. A compound as recited in claim 1 wherein $R^2$ is H; or a pharmaceutically acceptable salt thereof.

3. A compound as recited in claim 2 wherein $R^1$ is fluoro, chloro, bromo, $(C_1-C_2)$alkyl, or $(C_1-C_2)$fluoroalkyl; or a pharmaceutically acceptable salt thereof.

4. A compound as recited in claim 3 wherein $R^3$ is fluoro, chloro, or bromo; or a pharmaceutically acceptable salt thereof.

5. A compound as recited in claim 4 wherein $R^3$ is chloro; or a pharmaceutically acceptable salt thereof.

6. A compound as recited in claim 2 wherein $R^3$ is fluoro, chloro, or bromo; or a pharmaceutically acceptable salt thereof.

7. A compound as recited in claim 1 wherein $R^3$ is H; or a pharmaceutically acceptable salt thereof.

8. A compound as recited in claim 7 wherein $R^1$ is fluoro, chloro, bromo, $(C_1-C_2)$alkyl, or $(C_1-C_2)$fluoroalkyl; or a pharmaceutically acceptable salt thereof.

9. A compound as recited in claim 8 wherein $R^2$ is fluoro, chloro, or bromo; or a pharmaceutically acceptable salt thereof.

10. A compound selected from the group consisting of:

5-(5-chloro-4-fluoro 3-methylthiophen-2-yl)-1H-tetrazole;

5-(5-chloro-3-difluoromethylthiophen-2-yl)-1H-tetrazole;

5-(5-fluoro-3-methylthiophen-2-yl)-1H-tetrazole;

5-(5-chloro-3-methylthiophen-2-yl)-1H-tetrazole;

5-(3,5-dichlorothiophen-2-yl)-1H-tetrazole;

5-(4-bromo-3-methylthiophen-2-yl)-1H-tetrazole;

5-(4-bromo-3-ethylthiophen-2-yl)-1H-tetrazole; and 5-(4-chloro-3-ethylthiophen-2-yl)-1H-tetrazole;

or a pharmaceutically acceptable salt thereof.

11. A compound wherein the compound is

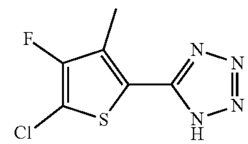

or a pharmaceutically acceptable salt thereof.

12. A compound wherein the compound is 5-(5-chloro-4-fluoro 3-methylthiophen-2-yl)-1H-tetrazole or a pharmaceutically acceptable salt thereof.

13. A compound wherein the compound is

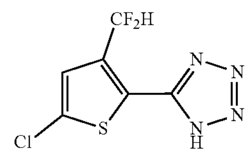 [SMILES: FC(F)c1cc(Cl)sc1-c1nnn[nH]1]

or a pharmaceutically acceptable salt thereof.

14. A compound wherein the compound is 5-(5-chloro-3-difluoromethylthiophen-2-yl)-1H-tetrazole or a pharmaceutically acceptable salt thereof.

15. A method of treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma comprising administering to a human in need of such treatment a therapeutically effective amount of a compound of claim 10 or a pharmaceutically acceptable salt of said compound.

16. The method as recited in claim 15 wherein nonalcoholic steatohepatitis is treated.

17. A method of treating heart failure, congestive heart failure, coronary heart disease, peripheral vascular disease, renovascular disease, pulmonary hypertension, vasculitis, acute coronary syndromes and modification of cardiovascular risk comprising administering to a human in need of such treatment a therapeutically effective amount of a compound of claim 10 or a pharmaceutically acceptable salt of said compound.

18. The method as recited in claim 17 wherein heart failure is treated.

19. A method of treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease comprising administering to a human in need of such treatment a therapeutically effective amount of a compound of claim 10 or a pharmaceutically acceptable salt of said compound.

20. The method as recited in claim 19 wherein Type II diabetes mellitus is treated.

21. A method of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma comprising administering to a human in need of such treatment a therapeutically effective amount of a compound of claim 10 or a pharmaceutically acceptable salt thereof.

22. The method as recited in claim 21 wherein hepatocellular carcinoma is treated.

23. A pharmaceutical composition which comprises a therapeutically effective amount of a compound of claim 10 or a pharmaceutically acceptable salt of said compound and a pharmaceutically acceptable carrier, vehicle or diluent.

24. A pharmaceutical combination composition comprising: a therapeutically effective amount of a composition comprising:

a first compound, said first compound being a compound of claim 10 or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluents.

25. The pharmaceutical combination composition as recited in claim 24 wherein said second compound is 4-(4-(1-isopropyl-7-oxo-1,4,6,7-tetrahydrospiro[indazole-5,4'-piperidine]-1'-carbonyl)-6-methoxypyridin-2-yl)benzoic acid; [(1R,5S,6R)-3-{2-[(2S)-2-methylazetidin-1-yl]-6-(trifluoromethyl)pyrimidin-4-yl}-3-azabicyclo[3.1.0]hex-6-yl] acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; (S)-2-(5-((3-ethoxypyridin-2-yl)oxy)pyridin-3-yl)-N-(tetrahydrofuran-3-yl)pyrimidine-5-carboxamide; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

26. The pharmaceutical combination composition as recited in claim 24 wherein said non-alcoholic steatohepatitis treatment agent or non-alcoholic fatty liver disease treatment agent is an ACC inhibitor, a KHK inhibitor, a DGAT-2 inhibitor, an FXR agonist, metformin, incretin analogs, or an incretin receptor modulator.

27. The pharmaceutical combination composition as recited in claim 24 wherein said anti-diabetic agent is an SGLT-2 inhibitor, metformin, incretin analogs, an incretin receptor modulator, a DPP-4 inhibitor, or a PPAR agonist.

28. The pharmaceutical combination composition as recited in claim 24 wherein said anti-diabetic agent is metformin, sitagliptin or ertugliflozin.

29. The pharmaceutical combination composition as recited in claim 24 wherein said anti-heart failure agent is an ACE inhibitor, an angiotensin receptor blocker, an angiotensin-receptor neprilysin inhibitor, a beta adrenergic receptor blocker, a calcium channel blocker, or a vasodilator.

30. A crystal comprising a compound having the structure:

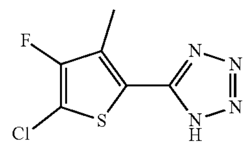

or a pharmaceutically acceptable salt thereof.

31. The crystal of claim 30 having a powder x-ray diffraction pattern comprising 2-theta values of (CuKα radiation, wavelength of 1.54056 Å) 10.6±0.2, 15.9±0.2, 23.5±0.2, and 32.1±0.2.

32. A crystal comprising a compound having the structure:

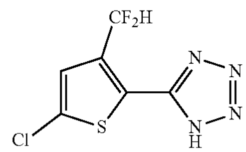 [SMILES: FC(F)c1cc(Cl)sc1-c1nnn[nH]1]

or a pharmaceutically acceptable salt thereof.

33. The crystal of claim 32 having a powder x-ray diffraction pattern comprising 2-theta values of (CuKα radiation, wavelength of 1.54056 Å) 24.5±0.2, 26.8±0.2, 33.9±0.2, and 39.1±0.2.

* * * * *